(12) United States Patent
Kadajji et al.

(10) Patent No.: US 11,633,405 B2
(45) Date of Patent: *Apr. 25, 2023

(54) STEROID HORMONE PHARMACEUTICAL FORMULATIONS

(71) Applicant: TherapeuticsMD, Inc., Boca Raton, FL (US)

(72) Inventors: Veeran Gowda Kadajji, Princeton, NJ (US); Mafruhul Bari, Boca Raton, FL (US); Annette Shadiack, Somerset, NJ (US); Thorsteinn Thorsteinsson, Boynton Beach, FL (US); Peter H. R. Persicaner, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/169,103

(22) Filed: Feb. 5, 2021

(65) Prior Publication Data

US 2021/0244747 A1 Aug. 12, 2021

Related U.S. Application Data

(60) Provisional application No. 62/971,743, filed on Feb. 7, 2020.

(51) Int. Cl.
*A61K 31/565* (2006.01)
*A61K 9/00* (2006.01)
*A61K 9/48* (2006.01)

(52) U.S. Cl.
CPC .......... *A61K 31/565* (2013.01); *A61K 9/0036* (2013.01); *A61K 9/4825* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | |
|---|---|---|
| 1,967,351 A | 7/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Reinhardt et al. |
| 3,526,648 A | 9/1970 | Daniel et al. |
| 3,710,795 A | 1/1973 | Higuchi et al. |
| 3,729,560 A | 4/1973 | Hagerman |
| 3,729,566 A | 4/1973 | Youngdale et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | Van Der Vies |
| 4,093,709 A | 6/1978 | Choi et al. |
| 4,154,820 A | 5/1979 | Simoons |
| 4,155,991 A | 5/1979 | Hartmann et al. |
| 4,196,188 A | 4/1980 | Besins |
| 4,215,691 A | 8/1980 | Wong |
| 4,237,885 A | 12/1980 | Pharriss et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |

(Continued)

FOREIGN PATENT DOCUMENTS

| CA | 2044371 A1 | 12/1991 |
|---|---|---|
| CA | 2612380 A1 | 12/2006 |

(Continued)

OTHER PUBLICATIONS

US 6,214,374 B1, 04/2001, Schmirler et al. (withdrawn)
Abbas, M.A., et al., "Regression of Endometrial Implants Treated with Vitamin D3 in A RatModel of Endometriosis," European Journal Of Pharmacology 715(1-3):72-75, Elsevier Science, Netherlands (2013).
Abitec, CapmuiMCM, EP, Technical Data Sheet, version 10, 2014, Columbus, OH.
Abitec, CapmuiMCM, NF, Technical Data Sheet, version 6, 2014, Columbus, OH.
Abitec, CapmuiMCM, Safley Data Sheet, 2011, Janesville, WI.
Abitec, CapmuiMCM, Technical Data Sheet, version 17, 2014, Columbus, OH.

(Continued)

*Primary Examiner* — Alton N Pryor

(74) *Attorney, Agent, or Firm* — Sterne, Kessler, Goldstein & Fox P.L.L.C.

(57) ABSTRACT

This disclosure provides pharmaceutical compositions for delivering estradiol to a subject in need thereof, as well as methods of administering the compositions, and methods of using them.

16 Claims, 3 Drawing Sheets

(56) References Cited

U.S. PATENT DOCUMENTS

| | | |
|---|---|---|
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,043,331 A | 8/1991 | Hirvonen et al. |
| 5,059,426 A | 10/1991 | Chiang et al. |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,164,416 A | 11/1992 | Nagai et al. |
| 5,208,225 A | 5/1993 | Boissonneault et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,295,945 A | 3/1994 | Miller |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,453,279 A | 9/1995 | Lee et al. |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 7/1997 | Lacy et al. |
| 5,653,983 A | 8/1997 | Meybeck et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon-Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |

(56) References Cited

U.S. PATENT DOCUMENTS

| | | |
|---|---|---|
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | De et al. |
| 6,190,331 B1 | 2/2001 | Caillouette |
| 6,201,072 B1 | 3/2001 | Rathi et al. |
| 6,217,886 B1 | 4/2001 | Önyüksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,262,115 B1 | 7/2001 | Guittard et al. |
| 6,267,984 B1 | 7/2001 | Beste et al. |
| 6,274,165 B1 | 8/2001 | Meconi et al. |
| 6,277,418 B1 | 8/2001 | Markaverich et al. |
| 6,283,927 B1 | 9/2001 | Caillouette |
| 6,284,263 B1 | 9/2001 | Place |
| 6,287,588 B1 | 9/2001 | Shih et al. |
| 6,287,693 B1 | 9/2001 | Savoir et al. |
| 6,291,527 B1 | 9/2001 | Giorgetti |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | De et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi-Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein et al. |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | De et al. |
| 6,599,519 B1 | 7/2003 | Seo et al. |
| 6,610,325 B1 | 8/2003 | Meignant et al. |
| 6,610,652 B2 | 8/2003 | Heaton et al. |
| 6,610,670 B2 | 8/2003 | Backensfeld et al. |
| 6,610,674 B1 | 8/2003 | Schreiber |
| 6,635,274 B1 | 10/2003 | Masiz et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,664,296 B1 | 12/2003 | Meignant |
| 6,682,757 B1 | 1/2004 | Wright |
| 6,692,763 B1 | 2/2004 | Cummings et al. |
| 6,708,822 B1 | 3/2004 | Muni |
| 6,716,454 B2 | 4/2004 | Meignant et al. |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Mas et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Huebner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Eini et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Daniels et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,987,129 B2 | 1/2006 | Mak et al. |
| 6,995,149 B1 | 2/2006 | Endrikat et al. |
| 7,004,321 B1 | 2/2006 | Palm et al. |
| 7,005,429 B2 | 2/2006 | Dey et al. |
| 7,011,846 B2 | 3/2006 | Shojaei et al. |

(56) References Cited

U.S. PATENT DOCUMENTS

| | | |
|---|---|---|
| 7,018,992 B2 | 3/2006 | Koch et al. |
| 7,030,104 B2 | 4/2006 | Gray et al. |
| 7,030,157 B2 | 4/2006 | Huazhu et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich et al. |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beaudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernas et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Bayly et al. |
| 8,182,833 B2 | 5/2012 | Hermsmeyer |
| 8,187,615 B2 | 5/2012 | Friedman |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Theone et al. |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,329,680 B2 | 12/2012 | Evans et al. |
| 8,337,814 B2 | 12/2012 | Osbakken et al. |
| 8,344,007 B2 | 1/2013 | Tang et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Bohler et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,415,332 B2 | 4/2013 | Diliberti et al. |
| 8,420,111 B2 | 4/2013 | Hermsmeyer |
| 8,435,561 B2 | 5/2013 | Besins et al. |
| 8,435,972 B2 | 5/2013 | Stein et al. |

(56) References Cited

U.S. PATENT DOCUMENTS

| | | |
|---|---|---|
| 8,449,879 B2 | 5/2013 | Laurent-Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Barrett et al. |
| 8,541,400 B2 | 9/2013 | Johnsson et al. |
| 8,551,462 B2 | 10/2013 | Goldstein et al. |
| 8,551,508 B2 | 10/2013 | Lee et al. |
| 8,557,281 B2 | 10/2013 | Halliday et al. |
| 8,568,374 B2 | 10/2013 | De et al. |
| 8,591,951 B2 | 11/2013 | Kohn et al. |
| 8,613,951 B2 | 12/2013 | Zale et al. |
| 8,633,178 B2 | 1/2014 | Bernick et al. |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmuller-Nethl et al. |
| 8,784,882 B2 | 7/2014 | Mattern |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,005,597 B2 | 4/2015 | Hansen et al. |
| 9,006,222 B2 | 4/2015 | Bernick et al. |
| 9,012,434 B2 | 4/2015 | Bernick et al. |
| 9,114,145 B2 | 8/2015 | Bernick et al. |
| 9,114,146 B2 | 8/2015 | Bernick et al. |
| 9,180,091 B2 * | 11/2015 | Bernick ................ A61K 31/565 |
| 9,248,136 B2 | 2/2016 | Bernick et al. |
| 9,289,382 B2 | 3/2016 | Bernick et al. |
| 9,301,920 B2 | 4/2016 | Bernick et al. |
| 9,931,349 B2 | 4/2018 | Shadiack et al. |
| 10,052,386 B2 | 8/2018 | Cacace et al. |
| 10,098,894 B2 | 10/2018 | Amadio et al. |
| 10,206,932 B2 | 2/2019 | Bernick et al. |
| 10,258,630 B2 | 4/2019 | Mirkin et al. |
| 10,398,708 B2 | 9/2019 | Mirkin et al. |
| 10,471,072 B2 | 11/2019 | Bernick et al. |
| 10,537,581 B2 * | 1/2020 | Bernick ................ A61K 31/57 |
| 10,568,891 B2 * | 2/2020 | Mirkin .................... A61K 9/02 |
| 10,806,697 B2 * | 10/2020 | Bernick ................ A61K 9/4858 |
| 10,835,487 B2 | 11/2020 | Bernick et al. |
| 10,888,516 B2 | 1/2021 | Bernick et al. |
| 11,065,197 B2 | 7/2021 | Bernick et al. |
| 11,116,717 B2 | 9/2021 | Bernick et al. |
| 11,123,283 B2 | 9/2021 | Bernick et al. |
| 11,241,445 B2 | 2/2022 | Bernick et al. |
| 11,246,875 B2 | 2/2022 | Bernick et al. |
| 11,266,661 B2 | 3/2022 | Mirkin et al. |
| 11,304,959 B2 | 4/2022 | Bernick et al. |
| 11,351,182 B2 | 6/2022 | Bernick et al. |
| 2001/0005728 A1 | 6/2001 | Guittard et al. |
| 2001/0009673 A1 | 7/2001 | Lipp et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | Deziegler et al. |
| 2001/0032125 A1 | 10/2001 | Bhan et al. |
| 2001/0034340 A1 | 10/2001 | Pickar |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Dittgen et al. |
| 2003/0049307 A1 | 3/2003 | Gyurik |
| 2003/0052799 A1 | 3/2003 | Weigl |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | Macleod et al. |
| 2003/0124182 A1 | 7/2003 | Shojaei et al. |
| 2003/0124191 A1 | 7/2003 | Besse et al. |
| 2003/0130558 A1 | 7/2003 | Mas et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |

(56) References Cited

U.S. PATENT DOCUMENTS

| | | |
|---|---|---|
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Grawe et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schly'Ter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou et al. |
| 2004/0073024 A1 | 4/2004 | Metcalf et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini-Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasy et al. |
| 2005/0021009 A1 | 1/2005 | Mas et al. |
| 2005/0025833 A1 | 2/2005 | Aschkenasy et al. |
| 2005/0031651 A1 | 2/2005 | Gervais et al. |
| 2005/0042173 A1 | 2/2005 | Besse et al. |
| 2005/0042268 A1 | 2/2005 | Aschkenasy et al. |
| 2005/0048116 A1 | 3/2005 | Straub et al. |
| 2005/0054991 A1 | 3/2005 | Tobyn et al. |
| 2005/0079138 A1 | 4/2005 | Chickering et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0216061 A1 | 9/2005 | Kim et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yang et al. |
| 2005/0239758 A1 | 10/2005 | Roby |
| 2006/0040904 A1 | 2/2006 | Ahmed et al. |
| 2007/0036843 A1 | 2/2007 | Hirsh et al. |
| 2007/0049567 A1 | 3/2007 | Wiley |
| 2007/0071777 A1 | 3/2007 | Bromer et al. |
| 2007/0191321 A1 | 8/2007 | Ahmed et al. |
| 2007/0270394 A1 | 11/2007 | El-Alfy et al. |
| 2009/0074859 A1 | 3/2009 | Patel |
| 2009/0136574 A1 | 5/2009 | Diaz-Astruc et al. |
| 2012/0065221 A1 | 3/2012 | Babul |
| 2012/0202695 A1 | 8/2012 | Toledano et al. |
| 2013/0150334 A1 | 6/2013 | Sun et al. |
| 2013/0338122 A1 | 12/2013 | Bernick et al. |
| 2013/0338123 A1 | 12/2013 | Bernick et al. |
| 2014/0088051 A1 | 3/2014 | Bernick et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100204 A1 | 4/2014 | Bernick et al. |
| 2014/0100205 A1 | 4/2014 | Bernick et al. |
| 2014/0213565 A1* | 7/2014 | Bernick ............... A61K 47/10 514/182 |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0133421 A1 | 5/2015 | Bernick et al. |
| 2015/0148323 A1 | 5/2015 | Cacace et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0297733 A1 | 10/2015 | Oberegger et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2018/0161343 A1* | 6/2018 | Mirkin ............... A61K 31/565 |
| 2018/0161344 A1* | 6/2018 | Mirkin ............... A61K 9/0034 |
| 2018/0161345 A1 | 6/2018 | Bernick et al. |
| 2018/0221389 A1 | 8/2018 | Amadio et al. |
| 2018/0256598 A1* | 9/2018 | Mirkin ............... A61K 9/4858 |
| 2018/0280410 A1 | 10/2018 | Amadio et al. |
| 2018/0289723 A1 | 10/2018 | Bernick et al. |

(56) References Cited

U.S. PATENT DOCUMENTS

| | | | |
|---|---|---|---|
| 2019/0022107 A1* | 1/2019 | Mirkin | A61K 9/02 |
| 2019/0046542 A1 | 2/2019 | Bernick et al. | |
| 2019/0070197 A1 | 3/2019 | Amadio et al. | |
| 2019/0142844 A1 | 5/2019 | Bernick et al. | |
| 2019/0247401 A1 | 8/2019 | Amadio et al. | |
| 2019/0343771 A1 | 11/2019 | Mirkin et al. | |
| 2019/0343845 A1 | 11/2019 | Bernick et al. | |
| 2019/0358243 A1* | 11/2019 | Mirkin | A61K 9/4825 |
| 2020/0069700 A1 | 3/2020 | Bernick et al. | |
| 2020/0171050 A1 | 6/2020 | Bernick et al. | |
| 2020/0230153 A1 | 7/2020 | Bernick et al. | |
| 2020/0230154 A1 | 7/2020 | Bernick et al. | |
| 2020/0276210 A1 | 9/2020 | Bernick et al. | |
| 2020/0281849 A1 | 9/2020 | Bernick et al. | |
| 2020/0297735 A1 | 9/2020 | Bernick et al. | |
| 2020/0297736 A1 | 9/2020 | Bernick et al. | |
| 2020/0323881 A1 | 10/2020 | Bernick et al. | |

FOREIGN PATENT DOCUMENTS

| | | |
|---|---|---|
| EP | 0261429 A1 | 3/1988 |
| EP | 0279977 A2 | 8/1988 |
| EP | 0750495 A1 | 1/1997 |
| EP | 0813412 B1 | 12/1999 |
| EP | 0904064 B1 | 10/2001 |
| EP | 1300152 A1 | 4/2003 |
| IN | 2005KO00053 | 8/2005 |
| JP | H02264725 A | 10/1990 |
| JP | H04503810 A | 7/1992 |
| JP | 2002510336 A | 4/2002 |
| JP | 2006513182 A | 4/2006 |
| RU | 2155582 C2 | 9/2000 |
| WO | WO-9010425 A1 | 9/1990 |
| WO | WO-9505807 A1 | 3/1995 |
| WO | WO-9712618 A1 | 4/1997 |
| WO | WO-9740823 A1 | 11/1997 |
| WO | WO-9841217 A1 | 9/1998 |
| WO | WO-9922680 A1 | 5/1999 |
| WO | WO-9952528 A1 | 10/1999 |
| WO | WO-9955333 A1 | 11/1999 |
| WO | WO-9962497 A1 | 12/1999 |
| WO | WO-0187276 A1 | 11/2001 |
| WO | WO-0191757 A1 | 12/2001 |
| WO | WO-2004032942 A1 | 4/2004 |
| WO | WO-2004054576 A1 | 7/2004 |
| WO | WO-2004105694 A2 | 12/2004 |
| WO | WO-2004110402 A1 | 12/2004 |
| WO | WO-2004110408 A2 | 12/2004 |
| WO | WO-2007076144 A2 | 7/2007 |
| WO | WO-2013078422 A2 | 5/2013 |
| WO | WO-2013112947 A1 | 8/2013 |
| WO | WO-2015179782 A1 | 11/2015 |
| WO | WO-2016018993 A1 | 2/2016 |

OTHER PUBLICATIONS

Abitec, CapmuiPG8, CAS No. 31565-12-5, version 11, 2006, Columbus, OH.
Abitec Corporation Excipients For The Pharmaceutical Industry—Regulatory And Product Information, 2 pages (2013).
Acarturk, F., "Mucoadhesive Vaginal Drug Delivery Systems," Recent patents on drug delivery & formulation 3(3):193-205, Bentham Science Publishers, United Arab Emirates (2009).
Acog, M., et al., "Practice Bulletin, Clinical Management Guidelines For Obstetrician-Gynecologists," Obstetrics & Gynecology, 141(123): 202-216, American College of Obstetrician and Gynecologists, United States (2014).
ACTIVELLA® (estradiol/ norethindrone acetate) prescribing information (Nov. 2017) FDA Label, 39 pages.
Advisory Action for U.S. Appl. No. 12/561,515, filed Sep. 17, 2021, dated Jan. 29, 2013, 3 pages.
Alabi, K. A., et al., "Analysis of Fatty Acid Composition of Thevetia peruviana and Huracrepitans Seed oils using GC-FID," Fountain Journal of Natural and Applied Sciences2(2):32-7, College of Natural and Applied Sciences, Fountain University, Nigeria (2013).
Alexander, KS, Corn Oil, CAS No. 8001-30-7, (2009).
Alvarez, P., et al., "Ectopic Uterine Tissue As A Chronic Pain Generator," Neuroscience 225:269-282, Elsevier Science, United States (2012).
Application Note JASCO CD Spectra of Pharmaceuticals Substances Steroids, 2 pages.
Araya-Sibaja, A.M., et al., "Morphology Study of Progesterone Polymorphs Prepared by Polymer-induced Heteronucleation (Pihn)," Scanning 35(4):213-221, John Wiley & Sons, United States (2013).
Araya-Sibaja, Andrea Manela, et al., "Chemical Properties of Progesterone Selected Refer," SciFinder, American Chemical Society & US National Library of Medicine, United States (2014).
Araya-Sibaja, Andrea Manela, et al., "Polymorphism in Progesterone," SciFinder, pp. 1-46, American Chemical Society & US National Library of Medicine, United States (2014).
Araya-Sibaja, Andrea Manela, et al., "Polymorphism in Progesterone Selected References," SciFinder, pp. 1-12, American Chemical Society & US National Library of Medicine, United States (2014).
ARAYA-SIBAJA., et al., "Crystallization of progesterone polymorphs using polymer-induced heteronucleation (PIHn) method," Drug Development and Industrial Pharmacy, Early Online, pp. 1-8, Informa Healthcare (2014).
Archer, D.F., et al., "Effects of Ospemifene on the Female Reproductive and Urinary Tracts: Translation From Preclinical Models into Clinical Evidence," Menopause, 22(7):786-796, Lippincott-Raven Publishers, United States (Jul. 2015).
Archer, F., et al., Estrace® vs Premarin® for Treatment of Menopausal Symptoms: Dosage Comparison Study 9(1):21-31, (1992).
Ashburn, A.D., et al., "Cardiovascular, Hepatic and Renal Lesions in Mice Receiving Cortisone, Estrone and Progesterone," The Yale Journal Of Biology and Medicine 35:329-340, Yale Journal of Biology and Medicine, United States (1963).
Azeem, A., et al., "Microemulsions as A Surrogate Carrier for Dermal Drug Delivery," Drug development and industrial pharmacy 35(5):525-547, Informa Healthcare, United Kingdom (2009).
Azure Pharma, Inc., "ELESTRIN—estradiol gel" Drug Info, http://dailymed.nlm.nih.gov/dailymed/archives/ fdaDrugInfo.cfm?archiveid= 11885, 26 pages, (2009).
Bakhmutova-Albert, E., et al.," Enhancing Aqueous Dissolution Rates of Progesterone via Cocrystallization," SSCI, Division of Aptuit, Poster No. R6247, West Lafayette.
Banerjee, S., et al., "on The Stability of Salivary Progesterone Under Various Conditions of storage," Steroids 46(6):967-974, Elsevier, United States (1985).
Barnett, S.M., et al., "Pressure-tuning infared and solution Raman spectroscopic studies of 17B-estradiol and several A-ring," Vibrational Spectroscopy 8:263, Elsevier Science B.V., Netherlands (1995).
Bartosova, L. and Bajgar, J., "Transdermal Drug Delivery in Vitro Using Diffusion Cells, "Current Medicinal Chemistry 19(27):4671-4677, Bentham Science Publishers, Netherlands (2012).
Bassi, P. and Kaur, G., "Innovations in Bioadhesive Vaginal Drug Delivery System," Expert Opinion on Therapeutic Patents 22(9):1019-1132, Informa Healthcare, United Kingdom (Sep. 2012).
Benbow, A.L. and Waddell, B.J., "Distribution and Metabolism of Maternal Progesterone in the Uterus, Placenta, and Fetus During Rat Pregnancy," Biology Of Reproduction 52(6):1327-1333, Society forthe Study of Reproduction, United States (1995).
Bernabei, M.T., et al., "[Release of Polymorphic forms of Progesterone From Dimethylpolysiloxane Matrices]," Bollettino chimico farmaceutico 122(1):20-26, Societa Editoriale Farmaceutica, Italy (1983).
Bhavnani, B.R. and Stanczyk, F.Z., "Misconception and Concerns About Bioidentical Hormones Used for Custom-Compounded Hormone Therapy," J Clin Endocrinol Metab, 97(3):756-759, Endocrine Society, United States (2012).
Bhavnani, B.R. and Stanczyk, F.Z., "Pharmacology of Conjugated Equine Estrogens: Efficacy, Safety and Mechanism of Action," The Journal of Steroid Biochemistry and molecular Biology 142:16-29, Pergamon, United Kingdom (2014).

(56) References Cited

OTHER PUBLICATIONS

Bhavnani, B.R., et al., "Structure Activity Relationships and Differential interactions and functional Activity of Various Equine Estrogens Mediated Via Estrogen Receptors (Ers) Eralpha and Erbeta," Endocrinology 149(10):4857-4870, Endocrine Society, United States (2008).
BioMed Central, Solubility of Progesterone in Organic Solvents, Online PDF, http://www.biomedcentral.com/content/supplementary/1475-2859-11-106-S2.pdf.
Blake, E.J., et al., "Single and Multidose Pharmacokinetic Study of A Vaginal Micronized Progesterone insert (Endometrin) Compared with Vaginal Gel in Healthy Reproductive-Aged Female Subjects," Fertility and Sterility 94(4):1296-1301, Elsevier for the American Society for Reproductive Medicine, United States (2010).
Borka, L., et al., "Crystal Polymorphism of Pharmaceuticals," Acta Pharma. Jugosl. 40:71-94, Croatian Pharmaceutical Society, Croatia (1990).
Branco C.C., et al., "Treatment of Atrophic Vaginitis," Therapy, 4(3):349-353, Future Medicine Ltd, United Kingdom (2007).
Brandstatter-Kuhnert, M., and Kofler, A., "Zur mikroskopischen Identitatsprufung und zur Polymorphie der Sexualhormone," Microchimica Acta 6:847-853, Springer-Verlag, Germany (1959).
Brared Christensson, J., et al., "Positive Patch Test Reactions To Oxidized Limonene: Exposure and Relevance," Contact Dermatitis 71(5):264-272, Wiley, United Kingdom (2014).
Brinton, L.A. and Felix, A.S., "Menopausal Hormone Therapy and Risk of Endometrial Cancer," The Journal Of Steroid Biochemistry And Molecular Biology 142:83-89, Pergamon, United Kingdom (2014).
"British Pharmacopoeia 2014 Online", Refined Maize Oil, Ph. Eur. Monograph 1342(1), Monographs: Medicinal and Pharmaceutical Substances, accessed at http:/www.pharmacopoeia.co.uklbp2014/ixbin/bp.egi?a=print&id=7400&tab=a-z%20index[Feb. 3, 2014 1:37:50 PM], accessed Feb. 3, 2014.
Burry, K.A., et al., "Percutaneous Absorption of Progesterone in Postmenopausal Women Treated with Transdermal Estrogen," American Journal Of Obstetrics And Gynecology180(6Pt1):1504-1511, Elsevier, United States (1999).
Busetta, P.B., and Hospital, M.,"Structure Cristalline et Moleculair de l'Oestradiol Hemihydrate," Acta Cryst B28:560-567, IUCr/Wiley, United Kingdom (1972).
Busetta,P.B., et al., "Structure Cristalline et Moleculaire du Complexe Oestradiol-Propanol," Acta Cryst. B28:1349, IUCr/Wiley, United Kingdom (1972).
Campsteyn, H., et al., "Structure Cristalline et Moleculaire de la Progesterone C21H3002," Acta Cryst. B28:3032-3042, IUCr/Wiley, United Kingdom (1972).
Cendejas-Santana, G., et al., "Growth and characterization of progesterone crystallites," Revista Mexicana de Fisica 50 S(1): 1-3, Sociedad Mexicana de Física, A. C., Mexico (2004).
Chambin, O and Jannin, V., "Interest of Multifunctional Lipid Excipients: Case Of Gelucire 44/14," Drug Development and Industrial Pharmacy, 31(6):527-534, Informa Healthcare, United Kingdom (Jul. 2005).
ChemPro, Top-Notch Technology in Production of Oils and Fats, Chempro-Edible-Oil-Refining-ISO-TUV-Austria, 3 pages.
Cho, Y.A and Gwak, H.S, "Transdermal Delivery of Ketorolac Tromethamine: Effects of vehicles and Penetration Enhancers," Drug Development and Industrial Pharmacy 30(6):557-564, Informa, United Kingdom (Jul. 2004).
Christen, R.D., et al., "Phase I/Pharmacokinetic Study of High-Dose Progesterone and doxorubicin," Journal Of Clinical Oncology, 11(12):2417-2426, American Society of Clinical Oncology, United States (1993).
Christensson, J.B., et al., "Limonene Hydroperoxide Analogues Differ in Allergenic Activity," Contact Dermatitis 59(6):344-352, Blackwell Munksgaard, United Kingdom (2008).
Christensson, J.B., et al., "Limonene Hydroperoxide Analogues Show Specific Patch Test Reactions," Contact Dermatitis 70(5):291-299, Wiley, United Kingdom (2014).
Chun, M-K., et al., "Transdermal Delivery of Estradiol and Norethindrone Acetate: Effect of Vehicles and Pressure Sensitive Adhesive Matrix," Journal of Korean Pharmaceutical Sciences 35(3):173-177, Springer, Netherlands (2005).
Cicinelli, E., et al., "Direct Transport of Progesterone From Vagina To Uterus," Obstetrics and Gynecology 95(3):403-406, Lippincott Williams & Wilkins, United States (2000).
Cicinelli, E., et al., "First uterine pass effect" is observed when estradiol is placed in the upper but not lower third of the vagina, Fertility and Sterility, 81(5): 1414-1416, Elsevier, Netherlands (2004).
Cicinelli, E., et al., "Placement of the Vaginal 17beta-estradiol Tablets in the Inner or Outer One Third of the Vagina Affects the Preferential Delivery of 17beta-estradiol Toward the Uterus or Periurethral Areas, Thereby Modifying Efficacy and Endometrial Safety," American Journal of Obstetrics and Gynecology 189(1):55-58, Elsevier, United States (Jul. 2003).
Cicinelli, E., "Intravaginal Oestrogen and Progestin Administration: Advantages and Disadvantages," Best Practice & Research Clinical Obstetrics & Gynecology, 22(2):391-405, Elsevier, Netherlands (Apr. 2008).
Committee Opinion, Incidentally Detected Short Cervical Length, Committee of Obstetric Practice, Obstetrics & Gynecology, Acog, vol. 119, No. 4, Apr. 2012, pp. 879-882.
Commodari, F., et al., "Comparison of 17β-estradiol structures from x-ray diffraction and solution NMR," Magnetic Resonance in Chemistry, 43:444-50, Wiley InterScience, United States (2005).
Cooper, A., et al., "Systemic Absorption of Progesterone From Progest Cream in Postmenopausal Women," Lancet 351(9111):1255-1256, Lancet Publishing Group, United Kingdom (1998).
O'Leary, P., et al., "Salivary, but not serum or urinary levels of progesterone are elevated after topical application of progesterone cream to pre- and postmenopausal women," Clin. Endocrinol. 53(5):615-620, Blackwell Science, United States (2000).
Corbett, S.H., et al., "Trends in Pharmacy Compounding for Women's Health in North Carolina: Focus on Vulvodynia," Southern Medical Journal 107(7):433-436, Southern Medical Association, United States (2014).
Crandall, C, "Vaginal Estrogen Preparations: a Review of Safety and Efficacy for Vaginal Atrophy," Journal of Women's Health, 11(10):857-877, Mary Ann Liebert, Inc, United States, (Dec. 2002).
Critchley, H.O., et al., "Estrogen Receptor Beta, but Not Estrogen Receptor Alpha, Is Present in the Vascular Endothelium of the Human and Nonhuman Primate Endometrium," The Journal Of Clinical Endocrinology and Metabolism 86(3):1370-1378, Endocrine Society, United States (2001).
Dauqan, E.M.A., et al., "Fatty Acids Composition of Four Different Vegetable Oils (Red Palm Olein, Palm Olein, Com Oil and Coconut Oil) by Gas Chromatography," IPCBEE, 14:31-34, 1ACSIT Press, Singapore (2011).
De Vries., et al, Guide to Good Prescribing: A Practical Manual, Essential Medicines and Health Products Information Portal, World Health Organization, Annex 3 ("How to explain the use of some dosage forms"), Checklist 11 ("Vaginal tablet without applicator") available at http://apps.who.int/medicinedocs/en/d/Jwhozip23e/7.3.11 html, 2 pages, 1994.
Dideberg, O., et al., "Crystal data on progesterone (C21H30O2), desoxycorticosterone (C21H30O3), corticosterone (C21H30O4) and aldosterone (C21H28O5H2O)," Journal of Applied Crystallography 4:80, Wiley, United States (1971).
Diramio, J.A., "Polyethylene Glycol Methacrylate/Dimetacrylate Hydrogels For Controlled Release Of Hydrophobic Drugs," The University of Georgia-Masters of Science Thesis, http://athenaeum.libs.uga.edu/bitstream/handle/10724/7820/diramio_jackie_a_200412_ms.pdf?sequence=1,131 pages, (2004).
Drakulic, B.J., et al., "Role of Complexes formation Between Drugs and Penetration Enhancers in Transdermal Delivery," International Journal Of Pharmaceutics 363(1-2):40-49, Elsevier/North-Holland Biomedical Press, Netherlands (2008).
Du, J.Y., et al., "Percutaneous Progesterone Delivery Via Cream Or Gel Application in Postmenopausal Women: A Randomized Cross-Over Study of Progesterone Levels in Serum, Whole Blood, Saliva,

(56) References Cited

OTHER PUBLICATIONS and Capillary Blood," Menopause 20(11): 1169-1175, Lippincott-Raven Publishers, United States (2013).

Duclos, R., et al., "Polymorphism of Progesterone: Influence of the carrier and of the solid dispersion manufacturing process. A calorimetric and radiocrystallographic study," Journal of Thermal Analysis 37:1869-1875, John Wiley & Sons, United Kingdom (1991).

Dugal, R., et al., "Comparison of Usefulness of Estradiol Vaginal Tablets and Estriol Vagitories for Treatment of Vaginal Atrophy," Acta Obstetricia Et Gynecologica Scandinavica 79(4):293-297, Wiley, United States (Apr. 2000).

Ebian, A.R., "Ebian Article: Polymorphism and solvation of ethinyl estradiol," Pharmaceutica Acta Helvetiae 54(4):111-114, Elsevier, Netherlands (1979).

Eisenberger, A. and Westhoff, C., "Hormone Replacement Therapy and Venous Thromboembolism," The Journal of steroid biochemistry and molecular biology 142:76-82, Pergamon, United Kingdom (Jul. 2014).

Engelhardt, H., et al., "Conceptus influences the Distribution of Uterine Leukocytes During Early Porcine Pregnancy," Biology Of Reproduction 66(6):1875-1880, Society for the Study of Reproduction, United States (Jun. 2002).

Ettinger, B., et al., "Comparison of Endometrial Growth Produced By Unopposed Conjugated Estrogens Or By Micronized Estradiol in Postmenopausal Women," American Journal Of Obstetrics and Gynecology 176(1 Pt1):112-117, Elsevier, United States (1997).

Ettinger, B., et al., "Measuring Symptom Relief in Studies of Vaginal and Vulvar Atrophy: the Most Bothersome Symptom Approach," Menopause, 15(5):885-889, North American Menopause Society, United States (Sep.-Oct. 2008).

Eugster-Hausmann, M., et al., "Minimized Estradiol Absorption With Ultra-low-dose 10 Microg 17beta-estradiol Vaginal Tablets," Climacteric, 13(3):219-227, Taylor & Francis, Untied Kingdom (Jun. 2010).

Excipients For Pharmaceuticals, Sasol Olefins & Surfactants GMBH, 28 pages (2010).

Faassen, F., et al., "Physicochemical Properties and Transport of Steroids Across Caco-2 Cells," Pharmaceutical research 20(2):177-186, Kluwer Academic/Plenum Publishers, United States (Feb. 2003).

"FDA, Draft Guidance on Progesterone," accessed at http://www.fda.gov/downloads/Drugs/GuidanceComplianceRegulatoryInformation/Guidances/UCM209294.pdf, accessed on (Recommended) Apr. 2010, (Revised) Feb. 2011.

Ferrari, R. A., et al., "Oxidative Stability of Biodiesel From Soybean Oil Fatty Acid Ethyl Esters," Scientia Agricola 62(3):291-95, Piracicaba, Brazil (2005).

Filipsson, F., et al., "Concise International Chemical Assessment Document 5," Limonene, first draft, World Health Organization, Geneva, 36 pages (1998).

Flyvholm, M.A. And Menne, T., "Sensitizing Risk of butylated Hydroxytoluene Based on Exposure and Effect Data," Contact Dermatitis 23(5):341-345, Wiley, United Kingdom (1990).

Fotherby. K., "Bioavailability of Orally Administered Sex Steroids Used in Oral Contraception and Hormone Replacement Therapy," Contraception 54(2):59-69, Elsevier, United States (1996).

Franklin, R.D. And Kutteh, W.H., "Characterization of Immunoglobulins and Cytokines in Human Cervical Mucus : influence of Exogenous and Endogenous Hormones," Journal Of Reproductive Immunology 42(2):93-106, Elsevier/North-Holland Biomedical Press, Ireland (1999).

Franz, T.J., et al., "Use of Excised Human Skin To Assess the Bioequivalence of Topical Products," Skin Pharmacology and Physiology 22(5):276-286, Karger, Switzerland (2009).

Freedman, R.R., "Menopausal Hot Flashes: Mechanisms, Endocrinology, Treatment," The Journal of steroid biochemistry and molecular biology 142:115-120, Pergamon, United Kingdom (Jul. 2014).

Fuchs, K.O., et al., "The Effects Of An Estrogen and Glycolic Acid Cream on the Facial Skin of Postmenopausal Women: A Randomized Histologic Study," Cutis 71(6):481-488, Frontline Medical Communications, United States (2003).

Fugh-Berman, A. and Bythrow, J., "Bioidentical Hormones for Menopausal Hormone Therapy: Variation on A Theme," Journal of general internal medicine 22(7):1030-1034, Springer, United States (2007).

Furness, S., et al., "Hormone therapy in Postmenopausal Women and Risk of Endometrial Hyperplasia," The Cochrane Database Of Systematic Reviews 8:1-204, Wiley, United Kingdom (2012).

Gafvert, E., et al., "Free Radicals in Antigen formation: Reduction of Contact Allergic Response To Hydroperoxides By Epidermal Treatment with Antioxidants," The British Journal Of Dermatology 146(4):649-656, Blackwell Scientific Publications, United Kingdom (2002).

Ganem-Quintanar., et al., "Evaluation of the transepidermal permeation of diethylene glycol monoethyl ether and skin water loss," International Journal of Pharmaceutics, 147(2):165-171, Elsevier, Netherlands (1997) Abstract Only.

Garad, S., et al., "Preclinical Development for Suspensions," A.K. Kulshreshtha et al. (eds.), Pharmaceutical Suspensions: From Formulation Development to Manufacturing, Springer, New York 2010, pp. 127-176.

Gattefossé SAS, Regulatory Data Sheet, Gelot 64, 6 pages (2012).

Gattefossé SAS, Regulatory Data Sheet, Lauroglycol 90, 5 pages (2012).

Gattefosse, "Excipients for Safe and Effective Topical Delivery," accessed at http://drug-dev.com/Main/Back-Issues/Transdermal-Topical-Subcutaneous-Noninvasive-Deliv-5.aspx# (2012).

Gattefosse SAS, Material Safety Data Sheet, Gelot 64, 8 pages (2012).

Geelen, M.J.H., et al., "Dietary Medium-Chain Fatty Acids Raise and (n-3) Polyunsaturated Fatty Acids Lower Hepatic Triacylglycerol Synthesis in Rats," The Journal of Nutrition 125:2449-2456, American Institute of Nutrition, United States (1995).

Gillet, J.Y., et al., "induction of Amenorrhea During Hormone Replacement therapy : Optimal Micronized Progesterone Dose A Multicenter Study," Maturitas 19(2):103-115, Elsevier/North Holland Biomedical Press, Ireland (1994).

Giron, D., "Thermal analysis and calorimetric methods in the characterisation of polymorphs and solvates," Thermochimica Acta 248:1-59, Elsevier B.V., Netherlands (1995).

Giron-Forest, D., et al., "Thermal Analysis Methods for Pharmacopoeial Materials," Journal of pharmaceutical and biomedical analysis 7(12):1421-1433, Elsevier Science, United Kingdom (1989).

Glaser, R.L., et al., "Pilot Study : Absorption and Efficacy of Multiple Hormones Delivered in A Single Cream Applied To the Mucous Membranes of the Labia and Vagina," Gynecologic and Obstetric Investigation 66(2):111-118,Basel, New York, Karger., Switzerland (2008).

Golatowski, C., et al., "Comparative Evaluation of Saliva Collection Methods for Proteome Analysis," International Journal Of Clinical Chemistry 419:42-46, Elsevier., Netherlands (2013).

Graham, J.D. And Clarke, C.L., "Physiological Action of Progesterone in Target Tissues," Endocrine Reviews 18(4):502-519, Endocrine Society, United States (1997).

Groothuis, P.G., et al., "Estrogen and the Endometrium : Lessons Learned From Gene Expression Profiling in Rodents and Human," Human Reproduction Update 13(4):405-417, Published for the European Society of Human Reproduction and Embryology by Oxford University Press, United Kingdom (2007).

Gullapalli, R.P., "Soft Gelatin Capsules (Softgels)," Journal of Pharmaceutical Sciences 99(10):4107-4148, Elsevier, United States (Oct. 2010).

Gurney, E.P., et al., "The Women"S Health initiative Trial and Related Studies: 10 Years Later: A Clinician"S View," The Journal of Steroid Biochemistry and Molecular Biology 142:42105, Pergamon, United Kingdom (2014).

Hamid, K.A., et al., "the Effects of Common Solubilizing Agents on the intestinal Membrane Barrier Functions and Membrane Toxicity in Rats," International Journal Of Pharmaceutics 379(1): 100-108, Amsterdam, Elsevier/North-Holland Biomedical Press., Netherlands (2009).

(56) References Cited

OTHER PUBLICATIONS

Hapgood, J.P., et al., "Potency of Progestogens Used in Hormonal Therapy: Toward Understanding Differential Actions," The Journal of Steroid Biochemistry and Molecular Biology 142:39-47, Pergamon, United Kingdom (2014).

Hargrove, J.T., et al., "Menopausal Hormone Replacement Therapy with Continuous Daily Oral Micronized Estradiol and Progesterone," Obstetrics and Gynecology 73(4):606-612, Lippincott Williams & Wilkins, United States (1989).

Haner B.A., and Norton, D.A., "Crystal data (I) for some pregnenes and pregnadienes," Acta Crystallographica 17:1610, International Union of Crystallography, United Kingdom (1964).

Hatton, J., et al., "Safety and Efficacy of A Lipid Emulsion Containing Medium-Chain Triglycerides," Clinical Pharmacy 9(5):366-371, American Society Of Hospital Pharmacists, United States (1990).

He, F., et al., "Apoptotic Signaling Pathways in Uteri of Rats with Endometrial Hyperplasia induced By Ovariectomy Combined with Estrogen," Gynecologic and Obstetric Investigation 76(1):51-56, Karger, Switzerland (2013).

Helbling, I.M., et al., "The Optimization of An intravaginal Ring Releasing Progesterone Using A Mathematical Model," Pharmaceutical research 31(3):795-808, Kluwer Academic/Plenum Publishers, United States (2014).

Helmy, A., et al., "Estrogenic Effect of Soy Phytoestrogens on the Utems of Ovariectomized Female Rats," Clinical Pharmacology & Biopharmaceutics S2:1-7, Omics Online, United States (2014).

Henderson, V.W., "Alzheimer S Disease: Review of Hormone Therapy Trials and Implications for Treatment and Prevention After Menopause," The Journal of steroid biochemistry and molecular biology 142:99-106, Pergamon, United Kingdom (2014).

Henriksen. T., et al., "An ENDOR Sturdy of Radiation-Induced Molecular Damage to Progesterone," Journal of Magnetic Resonance 63(2):333-342, Elsevier Inc., United States (1985).

Herman, A and Herman, A.P., "Essential oils and their constituents as skin penetration enhancer for transdermal drug delivery: a review," Journal of Pharmacy and Pharmacology 67(4):473-485, Royal Pharmaceutical Society, United Kingdom (2014).

Hitchcock, C.L and Prior, J.C, "Oral Micronized Progesterone for Vasomotor Symptoms—a Placebo-controlled Randomized Trial in Healthy Postmenopausal Women," Menopause, 19(8):886-893, Lippincot Williams & Wilkins, United States (Aug. 2012).

Hodis, H.N. and Mack, W.J., "Hormone Replacement Therapy and The association with Coronary Heart Disease and Overall Mortality: Clinical Application of The Timing Hypothesis," The Journal of Steroid Biochemistry and Molecular Biology 142:68-75, Pergamon, United Kingdom (2014).

Holm, R., et al., "Examination of Oral Absorption and Lymphatic Transport of Halofantrine in a Triple-cannulated Canine Model After Administration in Self-microemulsifying Drug Delivery Systems (Smedds) Containing Structured Triglycerides," European Journal of Pharmaceutical Sciences, 20(1):91-97, Elsevier, Netherlands (Sep. 2003).

Hosmer, Jaclyn et al., "Microemulsions Containing Medium-Chain Glycerides as Transdermal Delivery Systems for Hydrophilic and Hydrophobic Drugs," AAPS PharmSciTech 10(2):589-596, Springer Science, United States (Jun. 2009).

Hospital, M., et al., "X-Ray Crystallography of Estrogens and Their Binding To Receptor Sites," Molecular pharmacology 8(4):438-445, American Society for Pharmacology and Experimental Therapeutics, United States (1972).

Hostynek, J., et al., "Predictinga bsorptiono f fragrancee hemicalst hrough human skin," Journal of the Society of Cosmetic Chemists 46:221-229, Society of Cosmetic Chemists, United States (1995).

Hulsmann, S., et al., "Stability of Extruded 17 Beta-Estradiol Solid Dispersions," Pharmaceutical Development and Technology 6(2):223-229, Informa Healthcare, United Kingdom (2001).

Humberstone, A., et al., "Lipid-based vehicles for the oral delivery of poorly water soluble drugs," Advanced Drug Delivery Reviews 25:103-128, Elsevier, Netherlands (1997).

Hurn, P.D. And Macrae, I.M., "Estrogen As A Neuroprotectant in Stroke," Journal Of Cerebral Blood Flow and Metabolism 20(4):631-652, Nature Publishing Group, United States (2000).

Hyder, S.M., et al., "Synthetic Estrogen 17Alpha-Ethinyl Estradiol induces Pattern of Uterine Gene Expression Similar To Endogenous Estrogen 17Beta-Estradiol," The Journal Of Pharmacology and Experimental Therapeutics 290(2):740-747, American Society for Pharmacology and Experimental Therapeutics, United States (1999).

International Search Report and Written Opinion for International Application No. PCT/US14/61811, USPTO, United States, dated Jan. 21, 2015, 9 pages.

International Search Report and Written Opinion for International Application No. PCT/US15/42621, Korean Intellectual Property Office, Republic of Korea, dated Oct. 29, 2015, 14 pages.

International Search Report and Written Opinion of International Application No. PCT/US2015/023041, Korean Intellectual Property Office, Republic of Korea, dated Jun. 30, 2015, 14 pages.

International Search Report and written opinion for International Application No. PCT/US13/46442, USPTO, United States, dated Nov. 1, 2013, 10 pages.

International Search Report and written opinion for International Application No. PCT/US13/46443, USPTO, United States, dated Oct. 31, 2013, 11 pages.

International Search Report and written opinion for International Application No. PCT/US13/46444, USPTO, United States, dated Oct. 31, 2013, 10 pages.

International Search Report and written opinion for International Application No. PCT/US13/46445, USPTO, United States, dated Nov. 1, 2013, 9 pages.

International Search Report and Written Opinion for related International Application No. PCT/US13/023309, USPTO, United States, dated Apr. 9, 2013, 12 pages.

International Search report for corresponding International Application No. PCT/US12/66406, USPTO, United States, dated Jan. 24, 2013, 3 pages.

Johanson, G., "Toxicity Review of Ethylene Glycol Monomethyl Ether and its Acetate Ester," Critical Reviews in Toxicology 30(3):307-345, Informa Healthcare, United Kingdom (May 2000).

Johnson, S., Williams, and John, F.W. Keana , "Racemic Progesterone," Tetrahedron Letters 4(4):193-196, Pergamon Press Ltd., United Kingdom (1963).

Joshi, S.G., et al., "Detection and Synthesis of A Progestagen-Dependent Protein in Human Endometrium," Journal Of Reproduction and Fertility 59(2):273-285, Portland Press, United Kingdom (1980).

Kanno J., et al., "the Oecd Program To Validate the Rat Uterotrophic Bioassay To Screen Compounds for in Vivo Estrogenic Responses: Phase 1," Environmental Health Perspectives 109(8):785-794, N.C. National Institute of Environmental Health Sciences., United States (2001).

Karande, P., et al., "Enhancement of transdermal drug delivery via synergistic action of chemicals," Biochimica et Biophysica Acta, 1788:2362-2373, Elsevier, Netherlands (Sep. 2009).

Karlberg, A.T., et al., "Air Oxidation of D-Limonene (the Citrus Solvent) Creates Potent Allergens," Contact Dermatitis 26(5):332-340, Wiley, United Kingdom (1992).

Karlberg, A.T., et al., "influence of An Anti-Oxidant on the formation of Allergenic Compounds During Auto-Oxidation of D-Limonene," The Annals Of Occupational Hygiene 38(2):199-207, Oxford University Press, United Kingdom (1994).

Kaunitz, A.M., "Extended Duration Use of Menopausal Hormone therapy," Menopause 21(6):679-681, Lippincott-Raven Publishers, United States (2014).

Khalil, S.A.H., "Stability and Dissolution Rates of Corticosteroids in Polyethylene Glycol Solid Dispersions," Drug Development and Industrial Pharmacy 10(5):771-787, Marcel Dekker, United States (1984).

Kharode, Y., et al., "the Pairing of A Selective Estrogen Receptor Modulator, Bazedoxifene, with Conjugated Estrogens As A New Paradigm for the Treatment of Menopausal Symptoms and Osteoporosis Prevention," Endocrinology 149(12):6084-6091, Endocrine Society, United States (2008).

(56) References Cited

OTHER PUBLICATIONS

Kim, Y.W., et al., "Safety Evaluation and Risk Assessment of D-Limonene," Journal Of Toxicology and Environmental Health. Part B, Critical Reviews 16(1):17-38, Informa Healthcare, United Kigndom (2013).
Kincl, F.A., et al., "Increasing Oral Bioavailability of Progesterone by formulation," Journal of Steroid Biochemistiy 9(1):83-84, Pergamon Press, United Kingdom (1978).
Kingsuerg, S., et al., "Treating Dyspareunia Caused by Vaginal Atrophy: a Review of Treatment Options Using Vaginal Estrogen Therapy," International Journal of Women's Health 1:105-111, Dove Medical Press, New Zealand (Aug. 2010).
Knuth., et al., "Hydrogel delivery systems for vaginal and oral applications: Formulation and biological considerations," Advanced Drug Delivery Reviews, 11(1-2): 137-167, Elsevier, Netherlands (1993) Abstract Only.
Koga, K., et al., "Enhancing Mechanism of Labrasol on intestinal Membrane Permeability of the Hydrophilic Dmg Gentamicin Sulfate," European Journal Of Pharmaceutics and Biopharmaceutics : Official Journal Of Arbeitsgemeinschaft Fur Pharmazeutische Verfahrenstechnik E.V 64(1):82-91, Elsevier Science, Netherlands (2006).
Komm, B.S., et al., "Bazedoxifene Acetate : A Selective Estrogen Receptor Modulator with Improved Selectivity," Endocrinology 146(9):3999-4008, Endocrine Society, United States (2005).
Korkmaz, F., "Biophysical Studies of Progesterone-Model Membrane Interactions," A Thesis Submitted To The Graduate School Of Natural And Applied Sciences Of The Middle East Technical University, 143 pages (Sep. 2003).
Kotiyan, P.N. and Vavia, P.R., "Stability indicating Hptlc Method for The Estimation of Estradiol," Journal of Pharmaceutical and Biomedical Analysis 22(4):667-671, Elsevier Science, United Kingdom (2000).
Krzyminiewski, R., et al., "EPR Study of the Stable Radical in a y-Irradialed Single Crystal of Progesterone," Journal of Magnetic Resonance 46:300-305, Academic Press, United Kingdom (1982).
Kubli-Garfias, C., et al., "Ab initio calculations of the electronic structure of glucocorticoids," Journal of Molecular Structure, Theochem 454(2-3):267-275, Elsevier Science B.V., Netherlands (1998).
Kubli-Garfias, Carlos, "Ab initio study of the electronic structure of progesterone and related progestins," Journal of Molecular Structure, Theochem 425(1-2):171-179, Elsevier B.V., Netherlands (1998).
Kuhnert-Brandstaetier, M., Kofler, A., "Zur Unterscheidung von losungsmittelhaltigen pseudopolymorphen Kristallformen und polymorphen Modifikationen bei Steroidhormonen.11.," Mikrochimica Acta 1:127-139, Springer Nature, Austria (1968).
Kuhnert-Brandstaetter, M., and Linder, R., "Zur Hydratbildung bei Steroidhormonen," Sci. Pharm. 41(2):109-116, Multidisciplinary Digital Publishing Institute, Switzerland (1973).
Kuhnert-Brandstatier, M., "Thermo-microscopic and spectrophotometric: Determination of steroid hormones," Microchemical Journal 9:105-133, Elsevier, Inc., United States (1965).
Kumasaka, T., et al., "Effects of Various forms of Progestin on the Endometrium of the Estrogen-Primed, Ovariectomized Rat," Endocrine Journal 41(2):161-169, Japan Endocrine Society, Japan (1994).
Kuon, R.J., and Garfield, R.E., "Actions of Progestins forthe inhibition of Cervical Ripening and Uterine Contractions To Prevent Preterm Birth," Facts, Views &Amp; Vision In Obgyn 4(2):110-119, Flemish Society of Obstetrics & Gynaecology, Belgium (2012).
Kuon, R.J., et al., "A Novel Optical Method To Assess Cervical Changes During Pregnancy and Use To Evaluate the Effects of Progestins on Term and Preterm Labor," American Journal Of Obstetrics and Gynecology 205(1):82.e15-82.e20, Elsevier, United States (2011).
Kuon, R.J., et al., "Pharmacologic Actions of Progestins To inhibit Cervical Ripening and Prevent Delivery Depend on their Properties , the Route of Administration , and the Vehicle," American Journal Of Obstetrics and Gynecology 202(5):455.e1-455.e9, Elsevier, United States (2010).

Labrie, F., et al., "Intravaginal prasterone (DHEA) provides local action without clinically significant changes in serum concentrations of estrogens or androgens," Journal of Steroid Biochemistry & Molecular Biology 138:359-367, Elsevier, Netherlandss (2013).
Lacey Jr., J.V., "The WHI ten year's later: An epidemiologist's view," J. Steroid Biochem. Mol. Biol. 142:12-15, Elsevier, Netherlands (2013).
Lahiani-Skiba, M., et al., "Solubility and Dissolution Rate of Progesterone-Cyclodextrin-Polymer Systems," Drug Development and Industrial Pharmacy 32(9):1043-1058, Informa Healthcare, United Kingdom (2006).
Lancaster, R.W., et al., "The Polymorphism of Progesterone: Stabilization of A "Disappearing" Polymorph by Co-Crystallization," Journal of Pharmaceutical Sciences 96(12):3419-3431, Wiley-Liss, United States (2007).
Land, L.M., et al., "The influence of water content of triglyceride oils on the solubility of steroids," Pharmaceutical Research 22(5):784-788, Springer Science+Business Media, United States (2005).
Lane, M.E., "Skin penetration enhancers," International Journal of Pharmaceutics 447:12-21, Elsevier, Netherlands (Feb. 2013).
Lanigan, R.S., and Yamarik, T.A., "Final Report on the Safety Assessment of Bht (1)," International Journal Of Toxicology 21(2):19-94, Sage Publications, United States (2002).
Lapez-Belmonte, J., et al., "Comparative Uterine Effects on Ovariectomized Rats After Repeated Treatment with Different Vaginal Estrogen formulations," Maturitas 72(4):353-358, Elsevier/North Holland Biomedical Press, Ireland (2012).
Lauer, A.C., et al., "Evaluation of the Hairless Rat as a Model for in Vivo Percutaneous Absorption," Journal of Pharmaceutical Sciences 86(1):13-18, Wiley-Liss, United States (1997).
Ley, L., et al., "Physicochemical properties of Progesterone," American Chemical Society & U.S. National Library of Medicine, Feb. 2014, 26 pages.
Leonetti, H.B., et al., "Topical Progesterone Cream Has An Antiproliferative Effect on Estrogen-Stimulated Endometrium," Fertility and sterility 79(1):221-222, Elsevier for the American Society for Reproductive Medicine, United States (2003).
Leonetti, H.B., et al., "Transdermal Progesterone Cream As An Alternative Progestin in Hormone therapy," Alternative Therapies In Health and Medicine 11(6):36-38, InnoVision Communications, United States (2005).
Lewis, J.G., et al., "Caution on The Use of Saliva Measurements To Monitor Absorption of Progesterone From Transdermal Creams in Postmenopausal Women," Maturitas 41(1):1-6, Elsevier/North Holland Biomedical Press, Ireland (2002).
Li, G.C., et al., "Solid-State Nmr Analysis of Steroidal Conformation of $17\hat{I}\pm$- and $17\hat{I}^2$-Estradiol in The Absence and Presence of Lipid Environment," Steroids 77(3):185-192, Elsevier, United States (2012).
Lindmark, T., et al., "Absorption Enhancement through Intracellular Regulation of Tight Junction Permeability by Medium Chain Fatty Acids in Caco-2 Cells," Journal of Pharmacology and Experimental Therapeutics 284(1):362-369, American Society for Pharmacology and Experimental Therapeutics, United States (1998).
Lindmark, T., et al., "Mechanisms of Absorption Enhancement by Medium Chain Fatty Acids in Intestinal Epithelial Caco-2 Cell Monolayers," Journal of Pharmacology and Experimental Therapeutics 275(2):958-964, American Society for Pharmacology and Experimental Therapeutics, United States (1995).
Lobo, R.A., "Foreword: Hormone Therapy Arms," The Journal of Steroid Biochemistry and Molecular Biology 142:3, Pergamon, United Kingdom (2014).
Lopes, L.B., et al., "Enhancement of transdermal delivery of progesterone using medium-chain mono and diglycerides as skin penetration enhancers," Pharmaceutical Development and Technology, 14:5, 524-529, Taylor & Francis, United Kingdom (Mar. 2009).
Lucy, M.C., et al., "Gonadotropin-releasing hormone at estrus: luteinizing hormone, estradiol, and progesterone during the periestrual and postinsemination periods in dairy cattle," Bioi Reprod 35(2):300-11, Oxford University Press, United Kingdom (1986) Abstract Only.
Lvova, M.H., et al., "Thermal Analysis in the Quality Control and Standardization of Some Drugs," Journal of Thermal Analysis 40:405-411, Wiley, United States (1993).

(56) References Cited

OTHER PUBLICATIONS

Mac Bride, M.B., et al., "Vulvovaginal Atrophy," Mayo Clinic Proceedings, 85(1):87-94, Elsevier, United Kingdom (Jan. 2010).
Madishetti, S.K., et al., "Development of Domperidone Bilayered Matrix Type Transdermal Patches : Physicochemical , in Vitro and Ex Vivo Characterization," Journal Of Faculty Of Pharmacy 18(3):221-229, BioMed Central, United Kingdom (2010).
Magness, R.R., and Ford, S.P., "Estrone, Estradiol-17 Beta and Progesterone Concentrations in Uterine Lymph and Systemic Blood Throughout The Porcine Estrous Cycle," Journal of Animal Science 57(2):449-455, American Society of Animal Science, United States (1983).
"Management of Symptomatic Vulvovaginal Atrophy: 2013 Position Statement of The North American Menopause Society," Menopause 20(9):888-902, Lippincott-Raven Publishers, United States (2013).
Manson, J.E., et al., "Menopausal Hormone Therapy and Health Outcomes During the Intervention and Extended Poststopping Phases of the Women's Health Initiative Randomized Trials," The Journal of the American Medical Association 310:1353-1368, American Medical Association, United States (2013).
March, Charles M. et al., "Roles of Estradiol and Progesterone in Eliciting the Midcycle Luteinizing Hormone and Follicle-Stimulating Hormone Surges," The Journal of Clinical Endocrinology & Metabolism, vol. 49, Issue 4, Oct. 1, 1979, pp. 507-513.
Martelli, Mary Elizabeth, Vaginal Medicine Administration, The Gale Encyclopedia of Nursing and Allied Health, Gale Group, 2002, pp. 2542-2543.
McGuffy, Irena, "Softgel Technology as a Lipid-Based Delivery Tool for Bioavailability Enhancement," Catalent Pharma Solutions Somerset, NJ (2011).
"Merck Index Online, Progesterone, Royal Society of Chemistry, accessed at https:1/www.rsc.org/Merck-IndeXImonograph/print/mono1500007889/progesterone?q=authorize, accessed on 2013 search Feb. 17, 2014,".
Mesley, R.J., "Clathrate formation From Steroids," Chemistry & industry 37:1594-1595, John Wiley & Sons Ltd., United Kingdom (1965).
Miles, R.A., et al., "Pharmacokinetics and Endometrial Tissue Levels of Progesterone After Administration By intramuscular and Vaginal Routes : A Comparative Study," Fertility and Sterility 62(3):485-490, Elsevier for the American Society for Reproductive Medicine, United States (1994).
Miller, J.A., et al., "Safety and Feasibility of Topical Application of Limonene As A Massage Oil To the Breast," Journal Of Cancer Therapy 3(5A), Scientific Research Publishing, United States (2012).
Monti, D., et al., "Effect of different terpene-containing essential oils on permeation of estradiol through hairless mouse skin," International Journal of Pharmaceutics, 237:209-24, Elsevier, Netherlands (2002).
Mueck, A.O., et al., "Genomic and Non-Genomic Actions of Progestogens in The Breast," J Steroid Biochem Mol Biol. 142:62-67, Pergamon Press, United Kingdom (2014).
Muramatsu, M., et al., "Thermodynamic Relationship between a- and B-Forms of Crystalline Progesterone," Journal of Pharmaceutical Sciences 68(2):175-178, American Pharmacists Association (1979).
Ng, J., et al., "Advances in biodiesel fuel for application in compression ignition engines," Clean Technologies and Environmental Policy 12:459-493, Springer-Verlag, Germany (2010).
Nicklas, M., et al., "Preparation and Characterization of Marine Sponge Collagen Nanoparticles and Employment for The Transdermal Delivery of 17Beta-Estradiol-Hemihydrate," Drug Dev Ind Pharm. 35(9):1035-1042, Informa Healthcare, United Kingdom (2009).
Nilsson, U., et al., "Analysis of Contact Allergenic Compounds in Oxidized d-Limonene," Chromatographia 42:199-205, Springer Vieweg, Germany (1996).
Notelovitz, M., et al., "Initial 17Beta-Estradiol Dose for Treating Vasomotor Symptoms," Obstetrics and Gynecology 95(5):726-731, Lippincott Williams & Wilkins, United States (2000).
Notice of Allowance dated Feb. 9, 2022, in U.S. Appl. No. 16/833,186, Bernick, B.A., et al., filed Mar. 27, 2020, 9 pages.
Notice of Allowance dated Oct. 7, 2020, in U.S. Appl. No. 16/833,213, Bernick, B. A., et al., filed Mar. 27, 2020, 5 pages.
Notice of Allowance dated Sep. 8, 2021, in U.S. Appl. No. 14/521,002, Bernick, B. A., et al., filed Oct. 22, 2014, 6 pages.
Notice of Allowance dated Sep. 11, 2013, in U.S. Appl. No. 12/561,515, Bernick, B. A., et al., filed Sep. 17, 2009, 12 pages.
Notice of Allowance dated Mar. 12, 2021, in U.S. Appl. No. 16/837,929, Bernick, B. A., et al., filed Apr. 1, 2020, 7 pages.
Notice of Allowance dated Mar. 12, 2021, in U.S. Appl. No. 16/837,933, Bernick, B. A., et al., filed Apr. 1, 2020, 5 pages.
Notice of Allowance dated Mar. 17, 2021, in U.S. Appl. No. 16/837,937, Bernick, B. A., et al., filed Apr. 1, 2020, 18 pages.
Notice of Allowance dated Aug. 21, 2020, in U.S. Appl. No. 16/834,844, Bernick, B. A., et al., filed Mar. 30, 2020, 6 pages.
Notice of Allowance dated Dec. 6, 2013 for U.S. Appl. No. 13/684,002, Bernick, B.A., et al., filed Nov. 21, 2012, 7 pages.
Notice of Allowance dated Dec. 10, 2014 in U.S. Appl. No. 14/099,562, Bernick, B.A., et al., filed Dec. 6, 2013, 10 pages.
Notice of Allowance dated Dec. 10, 2014 in U.S. Appl. No. 14/099,598, Bernick, B.A., et al., filed Dec. 6, 2013, 8 pages.
Notice of Allowance dated Dec. 15, 2014 in U.S. Appl. No. 14/099,623, Bernick, B.A., et al., filed Dec. 6, 2013, 9 pages.
Notice of Allowance dated Feb. 11, 2015 in U.S. Appl. No. 14/475,864, Bernick, B.A., et al., filed Sep. 3, 2014, 9 pages.
Notice of Allowance dated Feb. 13, 2015 in U.S. Appl. No. 14/475,814, Bernick, B.A., et al., filed Sep. 3, 2014, 6 pages.
Notice of Allowance dated Jan. 22, 2015 in U.S. Appl. No. 14/099,582, Bernick, B.A., et al., filed Dec. 6, 2013, 5 pages.
Notice of Allowance dated Jul. 14, 2014, in U.S. Appl. No. 14/099,545, Bernick, B.A., et al., filed Dec. 6, 2013, 9 pages.
Notice of Allowance dated Jul. 15, 2014, in U.S. Appl. No. 14/099,571, Bernick, B.A., et al., filed Dec. 6, 2013, 11 pages.
Notice of Allowance dated Nov. 26, 2014, in U.S. Appl. No. 14/099,612, Bernick, B.A., et al., filed Dec. 6, 2013, 12 pages.
Notice of Allowance dated Nov. 7, 2014, in U.S. Appl. No. 14/099,582, Bernick, B.A., et al., filed Dec. 6, 2013, 14 pages.
NuGen, "What is NuGen HP Hair Growth System?" accessed at http://www.skinenergizer.com/Nugen-HP-Hair-Growth-System-p/senusystem.htm, accessed on Mar. 7, 2013, 3 pages, undated.
NuGest 900™, accessed at http://www.thehormoneshop.net/nugest900.htm, accessed on Mar. 5, 2013, 4 pages, undated.
Office Action dated Apr. 30, 2021 for U.S. Appl. No. 16/834,780, Bernick, B., et al., filed Mar. 30, 2020, 12 pages.
Office Action dated Feb. 28, 2022 for U.S. Appl. No. 16/834,780, Bernick, B., et al., filed Mar. 30, 2020, 12 pages.
Office Action dated Oct. 8, 2021 for U.S. Appl. No. 16/834,780, Bernick, B., et al., filed Mar. 30, 2020, 12 pages.
Office Action dated Nov. 3, 2015 for U.S. Appl. No. 14/103,355, Aelwine, N., et al., filed Dec. 11, 2013, 7 pages.
Office Action dated Dec. 12, 2011 for U.S. Appl. No. 12/561,515, Bernick, B., et al., filed Sep. 17, 2009, 14 pages.
Office Action dated Oct. 26, 2012 for U.S. Appl. No. 12/561,515, Bernick, B., et al., filed Sep. 17, 2009, 14 pages.
Office Action dated Jan. 14, 2022 for U.S. Appl. No. 17/169,103, Kadajji, V., et al., filed Feb. 5, 2021, 22 pages.
Office Action, dated Feb. 1, 2016, in U.S. Appl. No. 14/690,955, Bernick, B., et al., filed Apr. 20, 2015, 9 pages.
Office Action dated Feb. 18, 2014 for U.S. Appl. No. 14/099,545, Bernick, B., et al., filed Dec. 6, 2013, 7 pages.
Office Action dated Mar. 20, 2013 for U.S. Appl. No. 13/684,002, Bernick, B., et al., filed Nov. 21, 2012, 14 pages.
Office Action dated Jul. 16, 2013 for U.S. Appl. No. 13/684,002, Bernick, B., et al., filed Nov. 21, 2012, 13 pages.
Office Action dated Apr. 1, 2020 for U.S. Appl. No. 14/521,002, Bernick, B., et al., filed Oct. 22, 2014, 6 pages.
Office Action dated Jan. 5, 2016 for U.S. Appl. No. 14/521,002, Bernick, B., et al., filed Oct. 22, 2014, 9 pages.

(56) References Cited

OTHER PUBLICATIONS

Office Action dated Jan. 6, 2017 for U.S. Appl. No. 14/521,002, Bernick, B., et al., filed Oct. 22, 2014, 13 pages.
Office Action dated Jul. 20, 2018 for U.S. Appl. No. 14/521,002, Bernick, B., et al., filed Oct. 22, 2014, 28 pages.
Office Action dated Jun. 3, 2019 for U.S. Appl. No. 14/521,002, Bernick, B., et al., filed Oct. 22, 2014, 12 pages.
Office Action dated Oct. 5, 2017 for U.S. Appl. No. 14/521,002, Bernick, B., et al., filed Oct. 22, 2014, 13 pages.
Office Action dated Apr. 5, 2021 for U.S. Appl. No. 16/677,831, Bernick, B., et al., filed Nov. 8, 2019, 9 pages.
Office Action dated Apr. 7, 2021 for U.S. Appl. No. 16/746,434, Bernick, B., et al., filed Jan. 17, 2020, 13 pages.
Office Action dated Apr. 8, 2021 for U.S. Appl. No. 16/833,188, Bernick, B., et al., filed Mar. 27, 2020, 15 pages.
Office Action, dated Apr. 14, 2015, in U.S. Appl. No. 14/125,554, Bernick, B.A., filed Dec. 12, 2013, 9 pages.
Office Action dated Apr. 30, 2021 for U.S. Appl. No. 16/875,030, Bernick, B., et al., filed May 15, 2020, 16 pages.
Office Action, dated Apr. 7, 2015, in U.S. Appl. No. 14/624,051, Bernick B.A., filed Feb. 17, 2015, 10 pages.
Office Action, dated Feb. 18, 2015, in U.S. Appl. No. 14/521,230, Bernick, B.A., filed Oct. 22, 2014, 8 pages.
Office Action dated Oct. 3, 2017 for U.S. Appl. No. 14/489,818, Konopka, D., et al., filed Jun. 4, 2015, 14 pages.
Office Action dated Jul. 10, 2020 for U.S. Appl. No. 16/837,937, Bernick, B., et al., filed Apr. 1, 2020, 13 pages.
Office Action dated Nov. 30, 2020 for U.S. Appl. No. 16/837,937, Bernick, B., et al., filed Apr. 1, 2020, 15 pages.
Office Action, dated Jul. 18, 2014, in U.S. Appl. No. 14/099,623, Bernick, B.A., filed Dec. 6, 2013, 12 pages.
Office Action, dated Jul. 2, 2014, in U.S. Appl. No. 14/099,562, Bernick, B.A., filed Dec. 6, 2013, 9 pages.
Office Action, dated Mar. 27, 2014, in U.S. Appl. No. 14/099,562, Bernick, B.A., filed Dec. 6, 2013, 8 pages.
Office Action dated Jul. 2, 2015, in U.S. Appl. No. 13/843,428, Bernick, B.A., filed Mar. 15, 2013, 9 pages.
Office Action, dated Jul. 3, 2014, in U.S. Appl. No. 14/099,598, Bernick, B.A., filed Dec. 6, 2013, 16 pages.
Office Action, dated Jun. 17, 2014, in U.S. Appl. No. 14/099,582, Bernick, B.A., filed Dec. 6, 2013, 14 pages.
Office Action dated Jun. 19, 2015, in U.S. Appl. No. 14/106,655, Bernick, B.A., filed Dec. 13, 2013, 11 pages.
Office Action dated Jun. 25, 2020 for U.S. Appl. No. 16/834,844, Bernick, B., et al., filed Mar. 30, 2020, 11 pages.
Office Action, dated Mar. 12, 2015, in U.S. Appl. No. 14/136,048, Bernick, B., et al., filed Dec. 20, 2013, 24 pages.
Office Action dated Nov. 27, 2020 for U.S. Appl. No. 16/837,929 Bernick, B., et al., filed Apr. 1, 2020, 14 pages.
Office Action dated Oct. 6, 2020 for U.S. Appl. No. 16/837,933 Bernick, B., et al., filed Apr. 1, 2020, 13 pages.
Office Action dated Feb. 4, 2021 for U.S. Appl. No. 16/837,933 Bernick, B., et al., filed Apr. 1, 2020, 15 pages.
Office Action, dated Oct. 1, 2014, in U.S. Appl. No. 14/475,814, Bernick, B., et al., filed Sep. 3, 2014, 6 pages.
Office Action, dated Oct. 2, 2014, in U.S. Appl. No. 14/475,864, Bernick, B., et al., filed Sep. 3, 2014, 6 pages.
Office Action dated Aug. 7, 2020, in U.S. Appl. No. 16/833,213, Bernick, B., et al., filed Mar. 27, 2020, 13 pages.
Office Action dated Jul. 30, 2014, in U.S. Appl. No. 14/099,612, Bernick, B., et al., filed Dec. 6, 2013, 12 pages.
Zava, D.T., et al., "Percutaneous absorption of progesterone," Maturitas 77:91-92, Elsevier/North Holland Biomedical Press, Ireland (2014).
Supplementary European Search Report for EP Application No. EP 13741053.6, Munich, Germany, dated Jul. 1, 2015, 1 page.
Supplementary European Search Report for EP Application No. EP 13807188.1, Munich, Germany, dated Nov. 23, 2015, 3 pages.
Palamakula, A., et al., "Preparation and in Vitro Characterization of Self-Nanoemulsified Drug Delivery Systems of Coenzyme Q10 Using Chiral Essential Oil Components" Pharmaceutical Technology 74-88, Advanstar Communications Inc., United States (2004).
Panay, N., et al., "The 2013 British Menopause Society & Women's Health Concern recommendations on hormone replacement therapy," Menopause International: The Integrated Journal of Postreproductive Health, published online May 23, 2013, Sage Publications, accessed at http:1/min,sagepub.com/content/early/2013/05/23/1754045313489645.1.
Panchagnula, R. and Ritschel, W.A., "Development and Evaluation of An intracutaneous Depot formulation of Corticosteroids Using Transcutol as A Cosolvent: in-Vitro, Ex-Vivo and in-Vivo Rat Studies," J Pharm Pharmacol. 43(9):609-614, Wiley, United Kingdom (1991).
Parasuraman, S., et al., "Blood Sample Collection in Small Laboratory Animals," J Pharmacol Pharmacother. 1(2):87-93, Medknow Publications and Media, India (2010).
Park, U.S., et al., "Solvent Effects on Physicochemical Behavior of Estradiols Recrystallized for Transdermal Delivery," Arch Pharm Res. 31(1):111-116, Pharmaceutical Society of Korea, South Korea (2008).
Park, J.S., et al., "Use of Cp/Mas Solid-State Nmr for The Characterization of Solvate Molecules within Estradiol Crystal forms," Eur. J. Pharm. Biopharm. 60(3):407-412, Elsevier Science, Netherlands (2005).
Parrish, D.A. and Pinkerton, A.A., "A New Estra-1,3,5(10)-Triene-3,17Beta-Diol Solvate: Estradiol-Methanol-Water (3/2/1)," Acta Crystallogr C 59(Pt2):o80-82, Wiley-Blackwell, United States (2003).
Patel, D., et al., "Transdermal Drug Delivery System: A Review," The Pharma Innovation, The Pharma Journal 1(4):66-75, AkiNik Publications, India (2012).
Payne, R.S., et al., "Examples of Successful Crystal Structure Prediction: Polymorphs of Primidone and Progesterone," Int. J. Pharm. 177(2):231-245, Elsevier/North-Holland Biomedical Press, Netherlands (1999).
Persson, Linda C, et al., "Physicochemical Properties of Progesterone Selecte," SciFinder 1-5, American Chemical Society & U.S. National Library of Medicine, United States (2014).
Pfaus, J.G., et al., "Selective Facilitation of Sexual Solicitation in the Female Rat By A Melanocortin Receptor Agonist," Proceedings Of The National Academy Of Sciences Of The United States Of America 101(27):10201-10204, National Academy of Sciences, United States (2004).
Pheasant, R., "Polymorphism of 17-Ethinylestradiol," J. Am. Chem. Soc. 72(9):4303-4304, American Chemical Society, United States (1950).
Pickles, V.R. "Cutaneous Reactions To injection of Progesterone Solutions into the Skin," British Medical Journal 2(4780):373-374, British Medical Association, United Kingdom (1952).
Pinkerton, J.V. and Thomas, S., "Use of Serms for Treatment in Postmenopausal Women," The Journal of Steroid Biochemistry and Molecular Biology 142:142-154, Pergamon Press, United Kingdom (2014).
Pinkerton, J.V., "What are the Concerns About Custom-Compounded "Bioidentical" Hormone Therapy?" Menopause 21(12):1298-1300, Lippincott-Raven Publishers, United States (2014).
Pisegna, G.L., "A High-pressure Vibrational Spectroscopic Study of Polymorphism in Steroids," Thesis, Department of Chemistry, McGill University, National Library of Canada, Canada (1999).
Portman, D., et al., "One-year treatment persistence with local estrogen therapy in postmenopausal women diagnosed as having vaginal atrophy," Menopause 22(11): 1197-1203, The North American Menopause Society, United States (2015).
Potluri, P., et al., "Mixed-micellar proliposomal systems for enhanced oral delivery of progesterone," Drug Delivery 13(3):227-232, Taylor & Francis, United Kingdom (2006).
Prajapati, H.N., et al., "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development," Pharm Res. 29(1): 285-305, Springer Science+Business Media, Germany (2012).

(56) References Cited

OTHER PUBLICATIONS

Prajapati, H.N., et al., "Effect of Difference in Fatty Acid Chain Lengths of Medium-Chain Lipids on Lipid/Surfactant/Water Phase Diagrams and Drug Solubility," J. Excipients Food Chem. 2(3):73-88, JEFC, United States (2011).
Prausnitz, M.R. And Langer, R., "Transdermal Drug Delivery," Nature Biotechnology 26(11):1261-1268, Nature America Publishing, United States (2008).
Price, S.L., "The Computational Prediction of Pharmaceutical Crystal Structures and Polymorphism," Adv Drug Deliv Rev 56(3):301-319, Elsevier Science Publishers, Netherlands (2004).
Product Safety Assessment, Diethylene Glycol Monoethyl Ether, The Dow Chemical Company Page, 5 Pages (2007).
Progynova TS 100, available online at file:I//C:!Users/Caii%20Family/Desktop/Progynova%20TS%20100%2012%20Patches_Pack%20%28Estradioi%20Hemihydrate%29.html, (2010).
PROMETRIUM® (progesterone, USP) prescribing information (Jun. 2009) FDA Label, 33 pages.
Provider Data Sheet, "About Dried Blood Spot Testing," ZRT Laboratory, 3 pages (2014).
Rahn, D.D., et al., "Vaginal Estrogen for Genitourinary Syndrome of Menopause: A Systematic Review," Obstetrics and Gynecology 124(6): 1147-1156, Lippincott Williams & Wilkins, United States (2014).
Rao, R., et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability 7(2): 95-107, Juniper Publishers, United States (2015).
Rao, R. and Rao, S., "Intra Subject Variability of Progesterone 200 mg Soft Capsules in Indian Healthy Adult Postmenopausal Female Subjects under Fasting Conditions," Journal of Bioequivalence & Bioavailability 6(4):139-143, Juniper Publishers, United States (2014).
Regidor, P.A., et al., "Progesterone in Peri-and Postmenopause: A Review," Thieme Obstetrics and Gynecology 74(11):995-1002, Georg Thieme Verlag, Germany, (Nov. 2014).
Reisman, S.A., et al., "Topical Application of the Synthetic Triterpenoid Rta 408 Protects Mice From Radiation-induced Dermatitis," Radiation Research 181(5):512-520, Radiation Research Society, United States (2014).
Restriction Requirement, dated Apr. 14, 2015, U.S. Appl. No. 13/843,428, Bernick, B.A., filed Mar. 15, 2013, 7 pages.
Restriction Requirement, dated Apr. 29, 2014, in U.S. Appl. No. 14/099,582, Bernick, B.A., filed Dec. 6, 2013, 9 pages.
Restriction Requirement, dated Dec. 5, 2014, in U.S. Appl. No. 14/125,554, Bernick, B.A., filed Dec. 12, 2013, 7 pages.
Restriction Requirement, dated Dec. 5, 2014, in U.S. Appl. No. 14/521,230, Bernick, B.A., filed Oct. 22, 2014, 9 pages.
Restriction Requirement, dated Jul. 3, 2014, in U.S. Appl. No. 14/106,655, Bernick, B.A., filed Dec. 13, 2013, 6 pages.
Restriction Requirement, dated Mar. 16, 2015, in U.S. Appl. No. 13/843,362, Bernick, B.A., filed Mar. 15, 2013, 7 pages.
Restriction Requirement, dated Mar. 20, 2014, in U.S. Appl. No. 14/099,612, Bernick, B.A., filed Dec. 6, 2013, 9 pages.
Restriction Requirement, dated Mar. 26, 2014, in U.S. Appl. No. 14/476,040, Bernick, B.A., filed Sep. 3, 2014.
Restriction Requirement, dated Mar. 28, 2014, in U.S. Appl. No. 14/099,571, Bernick, B.A., filed Dec. 6, 2013, 7 pages.
Restriction Requirement, dated May 13, 2014, in U.S. Appl. No. 14/099,598, Bernick, B.A., filed Dec. 6, 2013, 9 pages.
Restriction Requirement, dated Nov. 4, 2014, in U.S. Appl. No. 14/136,048, Bernick, B.A., filed Dec. 20, 2013, 7 pages.
Restriction/Election Requirement dated Mar. 5, 2014 for U.S. Appl. No. 14/099,623, Bernick, B., et al., filed Dec. 6, 2013, 9 pages.
Restriction/Election Requirement dated Feb. 20, 2014 for U.S. Appl. No. 14/099,562, Bernick, B., et al., filed Dec. 6, 2013, 6 pages.
Rioux, J.E., et al., "17beta-estradiol Vaginal Tablet Versus Conjugated Equine Estrogen Vaginal Cream to Relieve Menopausal Atrophic Vaginitis," Menopause 7(3):156-161, Lippincott-Raven Publishers, United States (May-Jun. 2007).
Rodriguez-Tenreiro, C., et al., "Cyclodextrin/carbopol Micro-scale Interpenetrating Networks (ms-IPNs) for Drug Delivery," Journal of Controlled Release 123(1):56-66, Elsevier Science Publishers, Netherlands (Oct. 2007).
Rodriguez-Tenreiro, C., et al., "Estradiol Sustained Release From High Affinity Cyclodextrin Hydrogels," European Journal of Pharmaceutics and Biopharmaceutics 66(1):55-62, Elsevier Science, Netherlands (Apr. 2007).
Rosilio, V., et al., "Physical Aging of Progesterone-Loaded Poly(D,L,-Lactide-Co-Glycolide) Microspheres," Pharmaceutical research 15(5):794-798, Kluwer Academic/Plenum Publishers, United States (1998).
Ross, D., et al., "Randomized, Double-Blind, Dose-Ranging Study of the Endometrial Effects of A Vaginal Progesterone Gel in Estrogen-Treated Postmenopausal Women," American Journal Of Obstetrics and Gynecology 177(4):937-941, Elsevier, Netherlands (1997).
Ruan, X. And Mueck, A.O., "Systemic Progesterone therapy—Oral, Vaginal, injections and Even Transdermal," Maturitas 79(3):248-255, Elsevier, Netherlands (2014).
Salem, H.F., "Sustained-Release Progesterone Nanosuspension Following intramuscular injection in Ovariectomized Rats," International Journal Of Nanomedicine 10:943-954, DOVE Medical Press, United Kingdom (2010).
Sallee, V.L., et al., "Determinants of intestinal mucosal uptake of short- and medium-chain fatty acids and alcohols," Journal of Lipid Research 14:475-484, American Society for Biochemistry and Molecular Biology, United States (1974).
Salole, E.G., "The Physicochemical Properties of Oestradiol," Journal of Pharmaceutical and Biomedical Analysis 5(7):635-648, Elsevier, Netherlands (1987).
Salole, E.G., "Estradiol," Analytical Profiles of Drug Substances 15:283-318, Elsevier, Netherlands (1986).
Santen, R.J., "Menopausal hormone therapy and breast cancer," J. Steroid Biochem. Mol. Biol. 142:52-61, Elsevier, Netherlands (2013).
Santen, R.J., "Vaginal Administration of Estradiol: Effects of Dose, Preparation and Timing on Plasma Estradiol Levels," Climacteric 18(2):121-134:1-14, Taylor & Francis, United Kingdom (2014).
Sarkar, B., et al., "Chemical Stability of Progesterone in Compounded Topical Preparations using PLO Transdermal CreamTM and HRT CreamTM Base," J. Steroids. Horm. Sci. 4:2, IOMC World, Belgium (2013).
Sarpal, K., et al., "Self-Emulsifying Drug Delivery Systems: A Strategy to Improve Oral Bioavailability," Current Research & Information on Pharmaceuticals Sciences 11(3):42-49, Empro, India (2010).
Sarrel. P.M., et al., "The Mortality Toll of Estrogen Avoidance: An Analysis of Excess Deaths Among Hysterectomized Women Aged 50 to 59 Years," Am. J. Public Health 103(9):1583-1588, American Public Health Association, United States (2013).
Satyanarayana, D., et al., "Aqueous Solubility Predictions of Aliphatic Alcohols, Alkyl Substituted Benzoates and Steroids," Asian Journal of Chemistry 9(3):418-426, Wiley-VCH, Germany (1997).
Scavarelli, R.M., et al., "Progesterone and Hydrate or Solvate," SciFinder 1-2, American Chemical Society, United States (2014).
Schindler, A.E., et al., "Classification and pharmacology of progestins," Maturitas 46S1:S7-S16, Elsevier Ireland Ltd., Ireland (2003).
Schindler, A.E., "The "Newer" Progestogens and Postmenopausal Hormone Therapy (Hrt)," The Journal of Steroid Biochemistry and Molecular Biology 142:48-51, Pergamon Press, United Kingdom (2014).
Schutte, S.C., et al., "A Tissue-Engineered Human Endometrial Stroma That Responds To Cues for Secretory Differentiation, Decidualization, and Menstruation," Fertility and Sterility 97(4):997-1003, Elsevier for the American Society for Reproductive Medicine, United States (2012).
Schweikart, K.M., et al., "Comparative Uterotrophic Effects of Endoxifen and Tamoxifen in Ovariectomized Sprague-Dawley Rats," Toxicologic Pathology 42(8):1188-1196, Sage Publications, United States (2014).

(56) References Cited

OTHER PUBLICATIONS

SciFinder Scholar Prednisone Chemical Properties, SciFinde, pp. 1-7, American Chemical Society & U.S. National Library of Medicine, United States (2014).
SciFinder Scholar Prednisone Physical Properties, SciFinder, pp. 1-10, American Chemical Society & U.S. National Library of Medicine, United States (2014).
SciFinder Scholar Progesterone Experimental Properties, SciFinder, pp. 1-9, American Chemical Society & U.S. National Library of Medicine, United States (2014).
Serantoni, F., et al., "4-Pregnen-3, 20-Dione (progesterone, form II)," Crystal Structure Communications 4(1):189-92, Università di Parma, Italy (1975).
Shao, R., et al., "Direct Effects of Metformin in the Endometrium: A Hypothetical Mechanism for the Treatment of Women with Pcos and Endometrial Carcinoma," Journal Of Experimental & Clinical Cancer Research 33:41, BioMed Central, United Kingdom (2014).
Sharma, H.C, et al., SciFinder Physical Properties of Progesterone Selected Refer, SciFinder, pp. 1-5, American Chemical Society & United States National Library of Medicine, United States (2014).
Shrier, L.A., et al., "Mucosal Immunity of the Adolescent Female Genital Tract," The Journal Of Adolescent Health 32(3):183-186, Elsevier, United States (2003).
Shufelt, C.L., et al., "Hormone Therapy Dose, Formulation, Route of Delivery, and Risk of Cardiovascular Events in Women: Findings From The Women's Health Initiative Observational Study," Menopause 21(3):260-266, Lippincott-Raven Publishers, United States (2014).
Siew, A, et al., "Bioavailability Enhancement with Lipid-Based Drug-Delivery Systems" Pharmaceutical Technology 28:30-31, Advanstar Communications Inc., United States (2014).
Sigma-Aldrich, "Progesterone-Water Soluble: powder, BioReagent, suitable for cell culture", MSDS, available on Apr. 6, 2014 accessed at http://www.sigmaaldrich.com/catalog/product/sigma/p7556.
Simon, J., et al., "Effective Treatment of Vaginal Atrophy with An Ultra-Low-Dose Estradiol Vaginal Tablet," Obstetrics and Gynecology 112(5):1053-1060, Lippincott Williams & Wilkins, United States (Nov. 2008).
Simon, J.A. "What If the Women's Health Initiative Had Used Transdermal Estradiol and Oral Progesterone instead?" Menopause 21(7):769-783, Lippincott-Raven Publishers, United States (2014).
Simon, J.A., et al., "A vaginal estradiol softgel capsule, TX-004HR, has negligible to very low systemic absorption of estradiol: Efficacy and pharmacokinetic data review," Maturitas 9951-58, Elsevier, Netherlands (2017).
Sitruk-Ware, R., et al., "Oral Micronized Progesterone—Bioavailability Pharmacokinetics, Pharmacological and Therapeutic Implications—A Review," Contraception 36(4):373-402, Elsevier, Netherlands (1987).
Sitruk-Ware, R., "Pharmacological profile of progestins," Maturitas 47:277-283, Elsevier Ireland Ltd., Ireland (2004).
Sitruk-Ware, R., "Progestogens in Hormonal Replacement Therapy: New Molecules, Risks, and Benefits," Menopause 9(1):6-15, Lippincott-Raven Publishers, United States (2002).
Smith, N.L., et al., "Lower Risk of Cardiovascular Events in Postmenopausal Women Taking Oral Estradiol Compared with Oral Conjugated Equine Estrogens," JAMA Intern Med. 174:25-31, American Medical Association, United States (2014).
Smyth, H.F., et al., "A 2-Yr Study of Diethylene Glycol Monoethyl Ether in Rats," Food and Cosmetics Toxicology 2:641-642, Pergamon Press, United Kingdom (1964).
Sofi, S.H., et al., "Gelucire: A Versatile Formulation Excipient," International Journal of Pharmacy & Pharmaceutical Research 10(3):55-73, Sagar: Innovare Academic sciences Pvt. Ltd., India (2017).
Stanczyk, F.Z., "All progestins are not created equal," Science 68:879-890, Elsevier, United States (2003).

Stanczyk, F.Z. And Bhavnani, B.R., "Current Views of Hormone Therapy for The Management and Treatment of Postmenopausal Women," J Steroid Biochem Mol Biol 142:1-2, Elsevier, Netherlands (2014).
Stanczyk, F.Z. And Bhavnani, B.R., "Use of Medroxyprogesterone Acetate for Hormone Therapy in Postmenopausal Women: Is It Safe?" J Steroid Biochem Mol Biol 142:30-38, Elsevier, Netherlands (Jul. 2014).
Stanczyk, F.Z., et al., "Ethinyl Estradiol and $17\hat{I}^2$-Estradiol in Combined Oral Contraceptives: Pharmacokinetics, Pharmacodynamics and Risk assessment," Contraception 87(6):706-727, Elsevier, United States (2013).
Stanczyk, F.Z., et al., "Percutaneous administration of progesterone: blood levels and endometrial protection," Menopause 12(2):232-237, The North American Menopause Society, United States (2005).
Stanczyk, F.Z., et al., "therapeutically Equivalent Pharmacokinetic Profile Across Three Application Sites for Ag200-15, A Novel Low-Estrogen Dose Contraceptive Patch," Contraception 87(6):744-749, Elsevier, United States (2013).
Stanczyk, F.Z., "Treatment of postmenopausal women with topical progesterone creams and gels: are they effective," Climacteric 17(Suppl 2):8-11, International Menopause Society, United Kingdom (2014).
Stefanick, M.L., "Estrogens and progestins: background and history, trends in use, and guidelines and regimens approved by the US Food and Drug Administration," Am. J. Med. 118 Suppl 12B:64-73, Elsevier, Netherlands (2005).
Stein, E.A., et al., "Progesterone Physical Properties," Scifinder 1-46, American Chemical Society & U.S. National Library of Medicine (2014).
Stephenson, K., "Transdermal Progesterone: Effects on Menopausal Symptoms and on Thrombotic, Anticoagulant, and Inflammatory Factors in Postmenopausal Women," International Journal of Pharmaceutical Compounding 12(4):295-304, International Journal of Pharmaceutical Compounding, United States (2008).
Strickley, R.G., "Solubilizing Excipients in Oral and injectable formulations," Pharmaceutical research 21(2):201-230, Kluwer Academic/Plenum Publishers, United States (2004).
Strocchi, A., "Fatty Acid Composition, and Triglyceride Structure of Corn Oil, Hydrogenated Corn Oil, and Corn Oil Margarine," Journal of Food Science 47:36-39, Wiley, United States (1981).
Struhar, M., et al., "Preparation of The Estradiol Benzoate Injection Suspension," Ceskoslovenska Farmacie 27(6):245-249, Ceskoslovenska Lekarska Spolecnost, Czech Republic (1978).
Sullivan, D.W., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier, Netherlands (2014).
Sun, J., "D-Limonene: Safety and Clinical Applications," Alternative Medicine Review 12(3):259-264, Alternative Medicine Review, United States (2007).
Tahitian Noni. "Body Balance Cream," Derechos Reservados Tahitian Noni International (2013), accessed at http://products.lni.com/dominican_republic/sa_spanish/nonistore/produc1/3438/3416/, 1 page, undated.
Tait, A.D., "Characterization of The Products From The Oxidation of Progesterone with Osmium Tetroxide," Steroids 20(5):531-542, Elsevier, Netherlands (1972).
Takacs, M., et al., "The Light Sensitivity of Corticosteroids in Crystalline form Photochemical Studies," Pharmaceutica acta Helvetiae 66(5-6):137-140, Schweizerische Apotheker-Verein, Switzerland (1991).
Tan, M.S., et al., "A Sensitive Method for the Determination of Progesterone in Human Plasma by LC-MS-MS," Abstract M1025 Cedra Corporation, United States (2013).
Tang, F.Y., et al., "Effect of Estrogen and Progesterone on the Development of Endometrial Hyperplasia in the Fischer Rat," Biology Of Reproduction 31(2):399-413, Society for the Study of Reproduction, United States (1984).
Tang, O.S., et al., "Pharmacokinetics of Different Routes of Administration of Misoprostol," Human Reproduction 17(2):332-336, Oxford University Press, United Kingdom (Feb. 2002).

(56) References Cited

OTHER PUBLICATIONS

Tas, M., et al., "Comparison of Antiproliferative Effects of Metformine and Progesterone on Estrogen-induced Endometrial Hyperplasia in Rats," Gynecological Endocrinology 29(4):311-314, Informa Healthcare, United Kingdom (2013).
Tella, S.H., et al., "Prevention and treatment of postmenopausal osteoporosis," The Journal of Steroid Biochemistry and Molecular Biology 142:155-170, Elsevier Ltd., United Kingdom (2014).
Thomas, J., et al., "The Effect of Water Solubility of Solutes on Their Flux Through Human Skin in Vitro: An Extended Flynn Database Fitted To The Roberts-Sloan Equation," International Journal of Pharmaceutics 339(1-2):157-167, Elsevier, Netherlands (2007).
Thomas, P., "Characteristics of Membrane Progestin Receptor Alpha (Mpralpha) and Progesterone Membrane Receptor Component 1 (Pgmrc1) and their Roles in Mediating Rapid Progestin Actions," Frontiers In Neuroendocrinology 29(2):292-312, Academic Press, United States (2008).
Tripathi, R., et al., "Study of Polymorphs of Progesterone by Novel Melt Sonocrystallization Technique: A Technical Note," AAPS PharmSciTech 11(3):1493-1498, Elsevier, Netherlands (2010).
Trommer, H. and Neubert, R.H., "Overcoming the Stratum Corneum: the Modulation of Skin Penetration A Review," Skin Pharmacology and Physiology 19(2):106-121, Karger, United States (2006).
Tuleu, C., et al., "Comparative Bioavailability Study in Dogs of a Self-Emulsifying Formulation of Progesterone Presented in a Pellet and Liquid form Compared with an Aqueous Suspension of Progesterone," Journal of Pharmaceutical Sciences 93(6):1495-1502, Wiley-Liss, United States (2004).
Ueda, T., et al., "Topical and Transdermal Drug Products," Pharmacopeial Forum 35(3):750-764, United States Pharmacopeial Convention, United States (2009).
UNC School of Pharmacy, "Preparation of Suppositories," PharmLabs. unc.edu, accessed at http://pharmlabs.unc.edu/labs/suppository/ inserting.htm on Apr. 6, 2021, 1 page.
USP, 401 Fats and Fixed Oils, Chemical Tests, Second Suplementto USP36-NF 31, pp. 6141-6151, (2013).
USP, Lauroyl Polyoxylglycerides, Saftey Data Sheet, US, 5611 Version #02, pp. 1-9, (2013).
USP, Official Monographs, Corn Oil, NF 31, pp. 1970-1971, (2013).
USP. Official Monographs, Lauroyl Polyoxylglycerides, NF 31, pp. 2064-2066, (2013).
USP, Official Monographs, Medium Chain Triglycerides, NF 31, pp. 2271-2272, (2013).
USP, Official Monographs, Mono- and Di-glycerides, NF 31, pp. 2101, (2013).
USP, USP Certificate-Corn Oil, Lot GOL404, Jul. 2013.
Utian, W.H., et al., "Relief of Vasomotor Symptoms and Vaginal Atrophy with Lower Doses of Conjugated Equine Estrogens and Medroxyprogesterone Acetate," Fertility and Sterility 75(6):1065- 1079, Elsevier for the American Society for Reproductive Medicine, United States (2001).
VAGIFEM® (estradiol vaginal tablets) prescribing information (Nov. 2009) FDA Label, 14 pages.
Voegtline, K.M. And Granger, D.A., "Dispatches From the interface of Salivary Bioscience and Neonatal Research," Frontiers In Endocrinology 5:25, Frontiers Research Foundation, Switzerland (2014).
Waddell, B.J. And Bruce, N.W., "The Metabolic Clearance of Progesterone in the Pregnant Rat: Absence of A Physiological Role for the Lung," Biology Of Reproduction 40(6):1188-1193, Society for the Study of Reproduction, United States (1989).
Waddell, B.J. And O'Leary, P.C., "Distribution and Metabolism of Topically Applied Progesterone in A Rat Model," The Journal of Steroid Biochemistry and Molecular Biology 80(4-5):449-455, Elsevier, Netherlands (2002).

Walter, L.M., et al., "The Role of Progesterone in Endometrial Angiogenesis in Pregnant and Ovariectomised Mice," Reproduction 129(6):765-777, BioScientifica, United Kingdom (2005).
Wang, H., et al., "Pharmacokinetics of Hard Micronized Progesterone Capsules via Vaginal or Oral Route Compared With Soft Micronized Capsules in Healthy Postmenopausal Women: a Randomized Open-label Clinical Study," Drug Des Devel Ther. 13:2475- 2482, Dove Press Limited, United Kingdom (Jul. 2019).
Wayne, C. and Julian, P., "A Study of the 22-Ketosteroids," Journal of the American Chemical Society 67(8):1369-1375, (1945).
Weber, E.J. "Corn Lipids," Cereal Chemistry Journal 55(5): 572- 584, American Association of Cereal Chemists (1978).
Weber, M.T., et al., "Cognition and Mood in Perimenopause: A Systematic Review and Meta-Analysis," The Journal of Steroid Biochemistry and Molecular Biology 142:90-98, Pergamon, United Kingdom (2014).
Weintraub, A., "Women Fooled By Untested Hormones From Compounding Pharmacies," Forbes, accessed at http://onforb.es/ 1L1Um1V, accessed on Feb. 23, 2015, 3 pages.
Whitehead, M.I., et al., "Absorption and Metabolism of Oral Progesterone," Br. Med. J. 280(6217):825-827, BMJ, United Kingdom (1980).
William, L., Duax, Jane F., Griffin, Douglas, C., Rohrer, "Conformation of Progesterone Side Chain: Conflict between X-ray Data and Force-Field Calculations," Journal of the American Chemical Society 103(22):6705-6712, (1981).
Wiranidchapong, C., et al., "Method of preparation does not affect the miscibility between steroid hormone and poly methacrylate," Thermochimica Acta 485(1-2):57-64, Elsevier B.V., Netherlands (2009).
Wood, C.E., et al., "Effects of estradiol with micronized progesterone or medroxyprogesterone acetate on risk markers for breast cancer in postmenopausal monkeys," Breast Cancer Research and Treatment 101:125-134, Springer Science+ Business Media B.V., United States (Jul. 2006).
Wren, B.G., et al., "Effect of Sequential Transdermal Progesterone Cream on Endometrium , Bleeding Pattern, and Plasma Progesterone and Salivary Progesterone Levels in Postmenopausal Women," The Journal Of The International Menopause Society 3(3):155-160, Informa Healthcare, United Kingdom (2000).
Wu, X., et al., "Gene Expression Profiling of the Effects of Castration and Estrogen Treatment in the Rat Uterus," Biology Of Reproduction 69(4):1308-1317, Society forthe Study of Reproduction, United States (2003).
Yalkowsky, Samuel, H., "Handbook of Acqueous Solubility Data," 1110-1111, CRC Press, United States.
Yalkowsky, S.H. And Valvani, S.C., "Solubility and Partitioning I: Solubility of Nonelectrolytes in Water," Journal of Pharmaceutical Sciences 69(8):912-922, Wiley-Liss, United States (1980).
Yue, W., et al., "Genotoxic Metabolites of Estradiol in Breast: Potential Mechanism of Estradiol induced Carcinogenesis," The Journal of Steroid Biochemistry and Molecular Biology 86(3-5):477- 486, Pergamon, United Kingdom (2003).
Zava, D. "Topical Progesterone Delivery and Levels in Serum, Saliva, Capillary Blood, and Tissues" Script:4-5 (2014).
Office Action dated Oct. 7, 2021 for U.S. Appl. No. 16/833,186, Bernick, B., et al., filed Mar. 27, 2020, 15 pages.
Opinion on the Diethylene Glycol Momoethyl Ether (DEGEE), Scientific Committee on Consumer Products, Dec. 19, 2006, 27 pages.
Outterson, K., "The Drug Quality and Security Act—Mind the Gaps," N. Engl. J. Med. 370(2):97-99, Massachusetts Medical Society, United States (2014).
Pachman, D.R. et al., "Management of menopause-associated vasomotor symptoms: Current treatment options, challenges, and future directions," Int. J. Womens Health. 2:123-135, Dove Medical Press, United Kingdom (2010).

\* cited by examiner

STEROID HORMONE PHARMACEUTICAL FORMULATIONS

FIELD

This disclosure provides pharmaceutical compositions comprising solubilized estradiol. Also provided are vaginally inserted soft capsules comprising the pharmaceutical compositions and methods of administering the soft capsules for the treatment of vulvovaginal atrophy and female sexual dysfunction.

BACKGROUND

Postmenopausal women frequently suffer from atrophic vaginitis or vulvar and vaginal atrophy (hereafter "vulvovaginal atrophy" or "VVA") with symptoms including, for example, vaginal dryness, vaginal odor, vaginal or vulvar irritation or itching, dysuria (pain, burning, or stinging when urinating), dyspareunia (vaginal pain associated with sexual activity), or vaginal bleeding associated with sexual activity. Other symptoms include soreness, urinary frequency and urgency, and urinary discomfort and incontinence ("estrogen-deficient urinary state(s)"). One symptom of vaginal atrophy is an increased vaginal pH, which creates an environment more susceptible to infections. The cytological examination of the vaginal mucosal epithelium in VVA subjects can also show signs of severe atrophy with a reduced number of superficial and intermediate cells an increased number of parabasal cells.

These symptoms are associated with decreased estrogenization of the vulvovaginal tissue and can even occur in women treated with oral estrogen-based pharmaceutical drug products. Although VVA is most common in postmenopausal women, it can occur at any time in a woman's life, and frequently interferes with sexual activity and satisfaction. Postmenopausal women with female sexual dysfunction (FSD) are almost four times more likely to have VVA than those without FSD.

Estrogen treatment has proven to be very successful in controlling menopausal symptoms, including VVA and FSD. Several studies have shown that the symptoms associated with vulvovaginal atrophy are often relieved by systemic or topical estrogen treatment.

SUMMARY

In a first aspect, the present disclosure provides a vaginal insert comprising a therapeutically effective amount of estradiol; and a solubilizing agent, wherein the solubilizing agent comprises at least one $C_2$-$C_5$ fatty acid or a glycol ester, monoglyceride, diglyceride, or triglyceride thereof.

In a first embodiment of the first aspect, the therapeutically effective amount of estradiol is from about 1 microgram to about 25 micrograms. In a second embodiment of the first aspect, the therapeutically effective amount of estradiol is from about 1 microgram to about 10 micrograms. In a third embodiment of the first aspect, the therapeutically effective amount of estradiol is about 4 micrograms. In a fourth embodiment of the first aspect, the therapeutically effective amount of estradiol is about 10 micrograms. In a fifth embodiment of the first aspect, the therapeutically effective amount of estradiol is about 25 micrograms.

In a sixth embodiment of the first aspect, the vaginal insert further comprises a second solubilizing agent selected from the group consisting of a mixture of PEG-6 stearate, ethylene glycol palmitostearate, and PEG-32 stearate; a mixture of hard fat, glyceryl ricinoleate, ceteth-20, and steareth-20; polyoxyl 40 hydrogenated castor oil USP; hard fat polyoxyl 20 cetostearyl ether; and combinations thereof. In a seventh embodiment of the first aspect, the second solubilizing agent is a mixture of PEG-6 stearate, ethylene glycol palmitostearate, and PEG-32 stearate.

In an eighth embodiment of the first aspect, the viscosity of the composition is about 5 cP to about 3000 cP at room temperature.

In a ninth embodiment of the first aspect, estradiol is the only active pharmaceutical ingredient in the vaginal insert.

In a tenth embodiment of the first aspect, the insert further comprises a capsule encapsulating the therapeutically effective amount of estradiol and the solubilizing agent. In an eleventh embodiment of the first aspect, the capsule is a soft gelatin capsule.

In a twelfth embodiment of the first aspect, the solubilizing agent comprises at least one $C_3$ fatty acid or a glycol mono- or di-ester thereof, a monoglyceride, diglyceride, or triglyceride thereof, or a combination of any of the foregoing.

In a second aspect, the present disclosure provides a vaginal insert comprising:
a therapeutically effective amount of estradiol;
a first solubilizing agent comprising one or more polyethylene glycol mono- or di-esters of a hydroxy $C_{16}$-$C_{26}$ fatty acid; and
a second solubilizing agent comprising a mixture of PEG-6 stearate, ethylene glycol palmitostearate, and PEG-32 stearate.

In a first embodiment of the second aspect, the therapeutically effective amount of estradiol is from about 1 microgram to about 25 micrograms. In a second embodiment of the second aspect, the therapeutically effective amount of estradiol is from about 1 microgram to about 10 micrograms. In a third embodiment of the second aspect, the therapeutically effective amount of estradiol is about 4 micrograms. In a fourth embodiment of the second aspect, the therapeutically effective amount of estradiol is about 10 micrograms. In a fifth embodiment of the second aspect, the therapeutically effective amount of estradiol is about 25 micrograms.

In a sixth embodiment of the second aspect, estradiol is the only active pharmaceutical ingredient in the vaginal insert.

In a seventh embodiment of the second aspect, the insert further comprises a capsule encapsulating the estradiol, the first solubilizing agent, and the second solubilizing agent. In an eighth embodiment of the second aspect, the capsule is a soft gelatin capsule.

In a third aspect, the present disclosure provides a vaginal insert comprising:
a therapeutically effective amount of estradiol;
a first solubilizing agent comprising propylene glycol monolaurate; and
a second solubilizing agent comprising polyoxyl 40 hydrogenated castor oil USP.

In a first embodiment of the third aspect, the therapeutically effective amount of estradiol is from about 1 microgram to about 25 micrograms. In a second embodiment of the third aspect, the therapeutically effective amount of estradiol is from about 1 microgram to about 10 micrograms. In a third embodiment of the third aspect, the therapeutically effective amount of estradiol is about 4 micrograms. In a fourth embodiment of the third aspect, the therapeutically effective amount of estradiol is about 10 micrograms. In a fifth embodiment of the third aspect, the therapeutically effective amount of estradiol is about 25 micrograms.

In a sixth embodiment of the third aspect, the viscosity of the composition is about 5 cP to about 3000 cP at room temperature.

In a seventh embodiment of the third aspect, estradiol is the only active pharmaceutical ingredient in the vaginal insert.

In an eighth embodiment of the third aspect, the insert further comprises a capsule encapsulating the estradiol, the first solubilizing agent, and the second solubilizing agent. In a ninth embodiment of the third aspect, the capsule is a soft gelatin capsule.

In a fourth aspect, the present disclosure provides a method of treating an estrogen-deficient state, comprising administering to a female in need thereof, a vaginal insert comprising a therapeutically effective amount of estradiol; and a solubilizing agent, wherein the solubilizing agent comprises at least one $C_2$-$C_5$ fatty acid or a glycol ester, monoglyceride, diglyceride, or triglyceride thereof. In a first embodiment of the fourth aspect, the estrogen-deficient state is vulvovaginal atrophy. In a second embodiment of the fourth aspect, the estrogen-deficient state is selected from the group consisting of vulvovaginal atrophy, dysuria, dyspareunia, estrogen-deficient urinary state, and vaginal bleeding associated with sexual activity.

In a third embodiment of the fourth aspect, administering the vaginal insert comprises administering the insert daily for two weeks, and twice weekly thereafter.

In a fifth aspect, the present disclosure provides a method of treating an estrogen-deficient state, comprising administering to a female in need thereof, a vaginal insert comprising:

a therapeutically effective amount of estradiol;

a first solubilizing agent comprising one or more polyethylene glycol mono- or di-esters of a hydroxy $C_{16}$-$C_{26}$ fatty acid; and a second solubilizing agent comprising a mixture of PEG-6 stearate, ethylene glycol palmitostearate, and PEG-32 stearate.

In a first embodiment of the fifth aspect, the estrogen-deficient state is vulvovaginal atrophy. In a second embodiment of the fifth aspect, the estrogen-deficient state is selected from the group consisting of vulvovaginal atrophy, dysuria, dyspareunia, estrogen-deficient urinary state, and vaginal bleeding associated with sexual activity.

In a third embodiment of the fifth aspect, administering the vaginal insert comprises administering the insert daily for two weeks, and twice weekly thereafter.

In a sixth aspect, the present disclosure provides a method of treating an estrogen-deficient state, comprising administering to a female in need thereof, a vaginal insert comprising:

a therapeutically effective amount of estradiol;

a first solubilizing agent comprising propylene glycol monolaurate; and a second solubilizing agent comprising polyoxyl 40 hydrogenated castor oil USP.

In a first embodiment of the sixth aspect, the estrogen-deficient state is vulvovaginal atrophy. In a second embodiment of the sixth aspect, the estrogen-deficient state is selected from the group consisting of vulvovaginal atrophy, dysuria, dyspareunia, estrogen-deficient urinary state, and vaginal bleeding associated with sexual activity.

In a third embodiment of the sixth aspect, administering the vaginal insert comprises administering the insert daily for two weeks, and twice weekly thereafter.

DETAILED DESCRIPTION

Definitions

Figure 1:
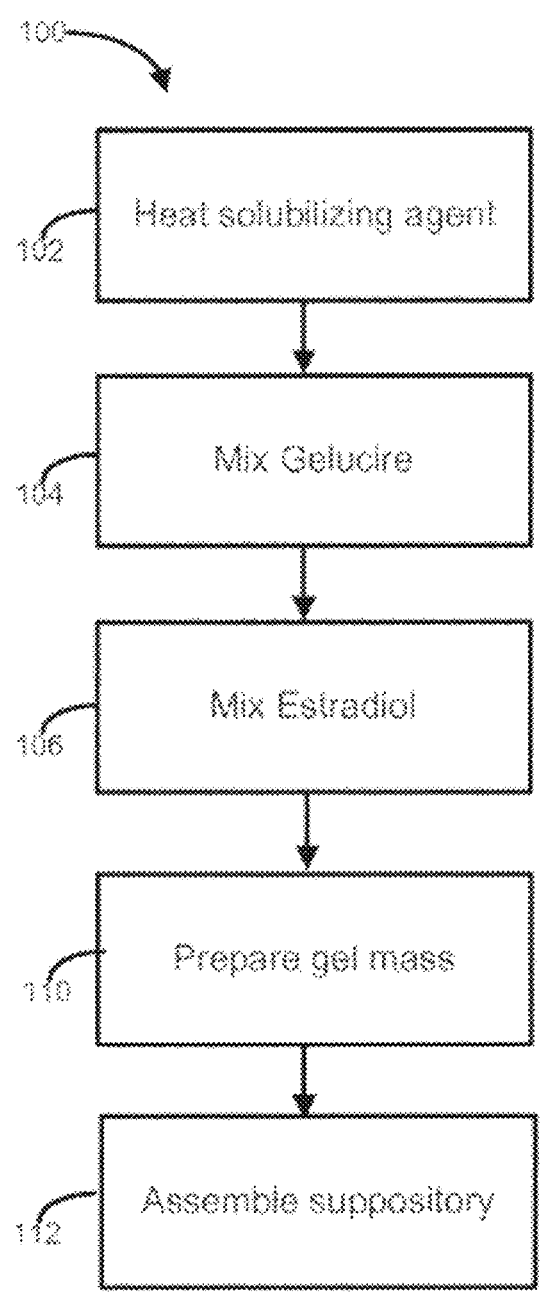
FIG. 1 depicts a flow diagram illustrating a process for preparing a vaginal insert.

The singular forms "a," "an," and "the" include plural referents unless the context clearly dictates otherwise.

As used herein, the term "or" is defined as a logical disjunction (i.e., and/or) and does not indicate an exclusive disjunction unless expressly indicated as such with the terms "either," "unless," "alternatively," and words of similar effect.

As used herein, the term "about" refers to 10% of the noted value, unless otherwise specified, and unless the upper bound of the range would exceed 100% of the pharmaceutical composition, in which case the upper limit of the range is limited to 99.9%. Thus, and by way of example only, a pharmaceutical composition including about 10 weight percent of a given compound could have from 9 to 11 weight percent of the compound. Similarly, a pharmaceutical composition including about 95 weight percent of a given compound could have from 85.5 to 99.9 weight percent of the compound in the pharmaceutical composition.

As used herein, the term "drug product" means at least one active pharmaceutical ingredient in combination with at least one excipient and provided in unit dosage form.

As used herein, the term "hormone deficiency" refers to a low level of one or more steroid hormones in a subject. Normal hormone levels will vary from subject to subject and can be determined via known methods. Low hormone levels may or may not be associated with symptoms including, for example and without limitation, vasomotor symptoms, sleep disturbances, mood changes, and vulvovaginal atrophy.

As used herein, the term "subject" refers to any animal, including humans.

The term "micronized" as used herein, refers to particles having an X50 particle size value below about 15 microns or having an X90 particle size value below about 25 microns. In some embodiments, a micronized particle can have an X90 particle size of less than 5 microns. The term "X50" means that one-half of the particles in a sample are smaller in diameter than a given number. For example, a micronized particle having an X50 of 5 microns means that, for a given sample of the micronized particle, one-half of the particles have a diameter of less than 5 microns. Similarly, the term "X90" means that ninety percent (90%) of the particles in a sample are smaller in diameter than a given number.

As used herein, the term "predominantly" means at least 50 percent. By way of example only, a compound comprising a linear predominantly C10 alkylene group, comprises at least 50 percent, at least 60 percent, at least 70 percent, at least 80 percent, at least 85 percent, at least 90 percent, at least 91 percent, at least 92 percent, at least 93 percent, at least 94 percent, at least 95 percent, at least 96 percent, at least 97 percent, at least 98 percent, or at least 99 percent of the linear C10 alkylene group, with the remainder being an alkylene group either greater than or less than C10. In certain embodiments, predominantly means at least 85 percent. "Predominantly" can be used in a variety of unit measurement systems, including mol %, w/w, or aggregate number of fatty acid esters, for example.

The term "glyceride" is an ester of glycerol (1,2,3-propanetriol) with acyl radicals of fatty acids and is known as an acylglycerol. If only one position of the glycerol molecule is esterified with a fatty acid, a "monoglyceride" or "monoacylglycerol" is produced; if two positions are esterified, a "diglyceride" or "diacylglycerol" is produced; and if all three positions of the glycerol are esterified with fatty acids, a "triglyceride" or "triacylglycerol" is produced. A glyceride is "simple" if all esterified positions contain the same fatty acid; whereas a glyceride is "mixed" if the esterified positions contained different fatty acids. The carbons of the glycerol backbone are designated sn-1, sn-2 and sn-3, with sn-2 being in the middle carbon and sn-1 and sn-3 being the end carbons of the glycerol backbone.

The term "solubilizing agent" refers to an agent or combination of agents that solubilize an active pharmaceutical ingredient (e.g., estradiol). Solubilizing agents include agents that solubilize or dissolve an active pharmaceutical ingredient to a desirable extent. Solubilizing agents suitable for use in the formulations disclosed herein are pharmaceutical grade solubilizing agents. It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc.

As used herein, the term "prevent" refers to the prophylactic treatment of a subject who is at risk of developing a condition (e.g., steroid hormone deficiency) resulting in a decrease in the probability that the subject will develop the condition.

The terms "treat," "treating," "treatment" and the like refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; or improving a subject's physical or mental well-being. The treatment or amelioration of symptoms can be based on objective or subjective parameters, including the results of a physical examination, neuropsychiatric examinations, or psychiatric evaluation.

The terms "atrophic vaginitis," "vulvovaginal atrophy," "vaginal atrophy," and "VVA" are used herein interchangeably. The cellular morphology of VVA is well known in the medical field.

As used herein, "sexual dysfunction" refers to a condition having one or more symptoms or difficulties involving one or more aspects of sexual activity. The dysfunction can prevent an individual from enjoying sexual activity. Non-limiting examples of symptoms of sexual dysfunction include, but are not limited to, dyspareunia, painful contractions (spasms) of the vaginal muscles, and problems with sexual desire, arousal, or orgasm. Sexual dysfunction can be lifelong (no effective performance) or acquired (after a period of normal function); and can be generalized or limited to certain situations or certain partners.

As used herein, "dyspareunia" refers to persistent or recurrent genital pain that occurs just before, during, or after sexual activity.

As used herein, "lubrication" refers to wetness in and around the vagina before, during, or after sexual activity. Increasing lubrication can include increasing the frequency of lubrication; decreasing the difficulty of becoming lubricated; and/or decreasing the difficulty in maintaining lubrication.

As used herein, "sexual desire" refers to the frequency of wanting to engage in sexual activity and/or the frequency of engaging in sexual activity as perceived by the individual. Sexual desire can be expressed, for example, in one or more cognitive activities, including the frequency of sexual thoughts, the extent of enjoyment of movies, books, music, etc. having sexual content and/or the extent of enjoyment or pleasure of thinking and fantasizing about sex as perceived by the individual.

As used herein, "sexual arousal" refers to the frequency of becoming sexually aroused, how readily sexual arousal occurs and/or if arousal is maintained, as perceived by the individual. Psychologically, arousal can include factors such as increased desire for sexual activity and excitement related to sexual activity. Physiologically, arousal can include increased blood flow to the genitals, causing clitoral engorgement, as well as vaginal lubrication.

As used herein, "orgasm" refers to the highest point of sexual excitement characterized by a subjective experience of intense pleasure marked normally by vaginal contractions in females. Increasing orgasm can include increasing the frequency, duration, and/or intensity of orgasms in a subject. Increasing orgasm can also include decreasing the difficulty of reaching orgasm.

As used herein, "satisfaction" refers to one or more positive emotions (e.g., contentment, fulfillment, gratification, and the like) related to a sexual activity or sexual relationship. Satisfaction can include, for example, satisfaction with occurrence of sexual arousal or orgasm, satisfaction with the amount of closeness with a partner, and satisfaction with overall sex life.

The phrase "therapeutically effective amount" refers to an amount of a pharmaceutical composition or of a given steroid hormone suitable to treat a particular symptom, disorder, or disease.

As used herein, the phrase "substantially" means at least about 90%, in certain embodiments, at least about 95%, and in still further embodiments, at least about 98%. For example, an object that is "substantially pure" or an object that is "substantially free" of another object, refers to a compound or composition that is at least about 90% pure by weight, at least about 95% pure by weight, or at least about 98% pure by weight and contains less than about 10% by weight, less than about 5% by weight or less than about 2% by weight of contaminants.

As used herein, the phrase "steroid hormone" refers to estradiol.

The term "bio-identical," "body-identical," or "natural" used in conjunction with the hormones disclosed herein, means hormones that match the chemical structure and effect of those that occur naturally or endogenously in the human body. An exemplary natural estrogen is 17β-estradiol.

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

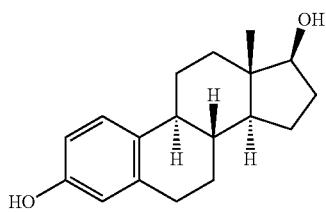

Estradiol is supplied in an anhydrous or hemi-hydrate form. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agent(s) or the formulations disclosed herein. Solubilized estradiol can include estradiol that is about 80% solubilized, about 85% solubilized, about 90% solubilized, about 95% solubilized, about 96% solubilized, about 97% solubilized, about 98% solubilized, about 99% solubilized, or about 100% solubilized. In some embodiments, the estradiol is "fully solubilized" with all or substantially all of the estradiol being solubilized or dissolved in the solubilizing agent. Fully solubilized estradiol can include estradiol that is about 97% solubilized, about 98% solubilized, about 99% solubilized or 100% solubilized. Solubility can be expressed as a mass fraction (% w/w, which is also referred to as weight percent (wt %)).

The solubility of a given steroid hormone can be measured using standard techniques by weighing a piece of filter paper, placing the weighed filter paper in a Buchner funnel (porcelain or glass with a glass frit), and drawing a known quantity of pharmaceutical composition through the filter paper using vacuum (such as with a side-arm flask fitted with a neoprene collar). After drying for an appropriate period of time (either at room temperature or at elevated temperature), the filter paper is reweighed. The amount of steroid hormone on the filter paper is calculated and the amount of soluble and insoluble steroid hormone is calculated.

The term "excipients," as used herein, refers to non-API ingredients such as solubilizing agents, anti-oxidants, oils, lubricants, and other agents used in formulating pharmaceutical products.

The term "active pharmaceutical ingredient" ("API") as used herein, means the active compound(s) used in formulating a drug product.

Pharmaceutical Compositions

Provided herein are pharmaceutical compositions comprising estradiol designed to be absorbed vaginally and have a local therapeutic effect (e.g., in vaginal and vulvar tissues). Generally, the pharmaceutical compositions disclosed herein are useful for treating VVA, dyspareunia, and other disorders caused by decreased estrogen presence.
Functionality
In certain embodiments, the pharmaceutical compositions disclosed herein can be alcohol-free or substantially alcohol-free. In certain embodiments, the pharmaceutical compositions disclosed herein can be encapsulated in soft gelatin capsules.
Estradiol
In certain embodiments, the pharmaceutical compositions disclosed herein are for vaginal insertion through a single dose or through multiple doses. In certain embodiments, the estradiol in the pharmaceutical compositions can be 100% solubilized. In certain embodiments, the estradiol in the pharmaceutical compositions can be less than 100% solubilized. In embodiments where the estradiol is less than 100% solubilized, the remaining estradiol can be present in a micronized (crystalline) form that is absorbable by the body and retains biological functionality, either in its micronized form or in another form which the micronized form is converted to after administration.

In certain embodiments, all or some of the estradiol can be solubilized in one or more solubilizing agents during manufacturing process. In certain embodiments, all or some of the estradiol can be solubilized following administration (e.g., insoluble estradiol in the formulation can be solubilized in a body fluid after administration). To the extent the estradiol is not fully solubilized at the time of administration/insertion, the estradiol will be substantially solubilized at a body temperature (average of 37° C.) and, generally, at the pH of the vagina (ranges from 3.8 to 4.5 in healthy subjects; or 4.6 to 6.5 in VVA subjects).

In certain embodiments, estradiol can be soluble in the solubilizing agent(s) at room temperature, although it can be desirable to warm certain solubilizing agents during manufacture to improve viscosity. In certain embodiments, the solubilizing agent can be a liquid or semi-solid. In certain embodiments, the solubilizing agent can be a liquid at between room temperature and about 50° C., at or below 50° C., at or below 40° C., or at or below 30° C.

In certain embodiments, the viscosity of the pharmaceutical compositions described this disclosure can range from about 5 centipose ("cP") to about 3000 cP at 25° C. A person of ordinary skill in the art can readily understand and select from suitable solubilizing agents to arrive at the desired viscosity. Viscosity can be measured by various types of viscosity meters and rheometers. These instruments measure the friction between the fluid and an adjacent layer. For example, a Brookfield Viscometer (DVEELVTJ0) can be used to measure the viscosity of these compositions by using an S31 spindle at 5-100 rpm and at room temperature.

In certain embodiments, the viscosity of the pharmaceutical compositions described in this disclosure will exceed 3000 cP, e.g., for semi-solids or solids. A person of ordinary skill in the art can readily measure the viscosity of such semi-solids or solids by using other known methods, e.g., increasing temperature or using different spindles.

In certain embodiments, the solubility of estradiol in the solubilizing agent(s) can be about 0.01 wt %, 0.02 wt %, 0.05 wt %, 0.06 wt %, 0.08 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, or higher. In some embodiments, the solubility of estradiol in the solubilizing agent(s) can be from about 0.001 wt % to about 5 wt %, from about 0.001 wt % to about 2 wt %, from about 0.001 wt % to about 1 wt %, from about 0.001 wt % to about 0.5 wt %, from about 0.001 wt % to about 0.1 wt %, from about 0.001 wt % to about 0.05 wt %, from about 0.01 wt % to about 5 wt %, from about 0.01 wt % to about 2 wt %, from about 0.01 wt % to about 1 wt %, from about 0.01 wt % to about 0.5 wt %, from about 0.01 wt % to about 0.1 wt %, from about 0.1 wt % to about 5 wt %, from about 0.1 wt % to about 2 wt %, from about 0.1 wt % to about 1 wt %, from about 0.1 wt % to about 0.5 wt %, from about 0.5 wt % to about 5 wt %, from about 0.5 wt % to about 2 wt %, from about 0.5 wt % to about 1 wt %, from about 1 wt % to about 5 wt %, from about 1 wt % to about 2 wt %, or from about 2 wt % to about 5 wt %.

In certain embodiments, the estradiol can be added to the pharmaceutical compositions disclosed herein as estradiol, estradiol hemihydrate, or any other estradiol form(s) suitable for use in pharmaceutical compositions or formulations.

The pharmaceutical compositions described herein can contain estradiol in varying amounts. Estradiol (or estradiol hemihydrate, for example, to the extent the water content of the estradiol hemihydrate is accounted for) can be present in the formulation in a dosage amount ranging from about 1 microgram (g) to about 50 µg. In other embodiments, the pharmaceutical composition can contain about: 1 µg, 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, or 50 µg estradiol (or an equivalent amount of, for example, estradiol hemihydrate). In certain embodiments, the pharmaceutical composition can contain about 2.5 µg, 4 µg, 6.25 µg, 7.5 µg, 12.5 µg, or 18.75 µg of estradiol. In certain embodiments, the pharmaceutical composition can contain from about 1 µg to about 10 µg, from about 3 µg to about 7 µg, from about 7.5 µg to 12.5 µg, from about 10 µg to about 25 µg, from about 1 µg, about 2.5 µg, from about 23.5 µg to about 27.5 µg, from about 7.5 µg to about 22.5 µg, or from about 10 µg to about 25 µg of estradiol. In one embodiment, the pharmaceutical composition comprises about 4 µg of estradiol. In one embodiment, the pharmaceutical composition comprises about 10 µg of estradiol. In another embodiment, the pharmaceutical composition comprises about 25 µg of estradiol.

In some embodiments, estradiol is the only active hormone in the vaginally inserted pharmaceutical composition.

Short Chain ($C_2$-$C_5$) Fatty Acids as Solubilizing Agents

In certain embodiments, the solubilizing agent can comprise at least one short chain fatty acid ($C_2$-$C_5$). In some embodiments, the short chain fatty acid can be acetic acid ($C_2$), propionic acid ($C_3$), butyric acid ($C_4$), isobutyric acid ($C_4$), valeric acid ($C_5$), isovaleric acid ($C_5$), or mixtures thereof.

In embodiments where the solubilizing agent comprises one or more $C_3$-$C_5$ short chain fatty acids, the one or more $C_3$-$C_5$ fatty acids can be saturated. In certain embodiments, the one or more $C_3$-$C_5$ short chain fatty acids can be predominantly saturated, i.e., greater than about 60% or greater than about 75% saturated.

In certain embodiments, the solubilizing agent can comprise one or more free short chain fatty acids, one or more short chain fatty acid ($C_2$-$C_5$) esters of glycerin, propylene glycol, ethylene glycol, or combinations thereof. Exemplary short chain fatty acid ($C_2$-$C_5$) esters of glycerin include, but are not limited to, monoacetylglyceride (MAG), diacetylglyceride (DAG), triacetin (triacetylglyceride, TAG), propionic triglyceride, monobutylglyceride, dibutylglyceride, butyric triglyceride (tributyrin), isobutyric triglyceride, isobutyric diglyceride, isobutyric monoglyceride, valeric triglyceride, valeric diglyceride, valeric monoglyceride, isovaleric monoglyceride, isovaleric diglyceride and isovaleric triglyceride. In some embodiments, the solubilizing agent can comprise triacetin.

In certain embodiments, the pharmaceutical composition can comprise a first solubilizing agent comprising at least one $C_2$-$C_5$ fatty acid or a glycol ester, monoglyceride, diglyceride, or triglyceride thereof and a second solubilizing agent. The second solubilizing agent can be any agent that solubilizes or dissolves the steroid hormone to the desirable extent.

In some embodiments, the second solubilizing agent can be TEFOSE 63 (mixture of PEG-6 stearate and ethylene glycol palmitostearate and PEG-32 stearate, available from GATTEFOSSÉ SAS, Saint-Priest, France), TEFOSE 1500 (mixture of PEG-6 stearate and PEG-32 stearate, available from GATTEFOSSÉ SAS, Saint-Priest, France), TEFOSE 2000 (mixture of PEG-6 stearate, ceteth-20, and stearath-20, available from GATTEFOSSÉ SAS, Saint-Priest, France), or GELOT 64 (mixture of PEG-75 stearate and glyceryl stearate, available from GATTEFOSSÉ SAS, Saint-Priest, France).

In certain embodiments, the second solubilizing agent can comprise one or more $C_6$-$C_{18}$ fatty acid PEG mono- or di-esters, one or more $C_6$-$C_{18}$ fatty acid mono-, di-, or tri-esters of glycerol, or combinations thereof. In one embodiment, the second solubilizing agent can be GELUCIRE 44/14 (lauroyl macrogol-32 glycerides (EP); lauroyl polyoxyl-32 glycerides (USP-NF)). Gelucire 44/14 is well known in the art and comprises a small fraction of mono-, di-, and triglycerides and a main fraction comprising PEG-32 (MW 1500) mono- and diesters of lauric acid (C12).

In certain embodiments, the second solubilizing agent can comprise a castor oil or hydrogenated castor oil ethoxylate. In particular embodiments, the castor oil or hydrogenated castor oil ethoxylate can be KOLLIPHOR EL (polyethoxylated castor oil, available from BASF), KOLLIPHOR RH40 (polyoxyl 40 hydrogenated castor oil USP, available from BASF), MYRJ 52 (polyoxyl 40 stearate, available from Spectrum Chemical), ETOCAS 40 (polyoxyethylene (40) castor oil, available from Croda), LABRASOL (caprylocaproyl polyoxyl-8-glycerides NF and caprylocaproyl macrogol-8-glycerides EP, available from GATTEFOSSÉ SAS, Saint-Priest, France), or CRODURET 60 (PEG 60 hydrogenated castor oil, available from Croda).

In certain embodiments, the second solubilizer can comprise OVUCIRE 3460 (a mixture of hard fat, glyceryl ricinoleate, ceteth-20, and steareth-20, available from GATTEFOSSÉ, Saint-Priest, France) or OVUCIRE WL 3264 (hard fat polyoxyl 20 cetostearyl ether, available from GATTEFOSSÉ, Saint-Priest, France).

In some embodiments, the weight:weight ratio of the first solubilizing agent to the second solubilizing agent can range from about 4:1 to about 10:1. In particular embodiments, the ratio of first solubilizing agent to second solubilizing agent is about 9:1.

In some embodiments, the pharmaceutical composition can comprise a first solubilizing agent comprising at least one $C_2$-$C_5$ fatty acid or a glycol ester, monoglyceride, diglyceride, or triglyceride thereof, and a second solubilizing agent comprising a mixture polyoxylglycerides and glycols. In particular embodiments, the pharmaceutical composition can comprise a 9:1 mixture of triacetin and TEFOSE 63 (mixture of PEG-6 stearate and ethylene glycol palmitostearate and PEG-32 stearate, available from GATTEFOSSÉ SAS, Saint-Priest, France).

Hydroxy Fatty Acids as Solubilizing Agents

In certain embodiments, the solubilizing agent can comprise at least one hydroxy fatty acid, such as at least one hydroxy $C_{16}$-$C_{26}$ fatty acid, at least one hydroxy $C_{16}$ to $C_{24}$ fatty acid, at least one hydroxy $C_{16}$ to $C_{22}$ fatty acid, at least one hydroxy $C_{16}$ to $C_{20}$, at least one hydroxy $C_{16}$ to $C_{18}$ fatty acid, at least one hydroxy $C_{18}$ to $C_{26}$ fatty acid, at least one hydroxy $C_{18}$ to $C_{24}$ fatty acid, at least one hydroxy $C_{18}$ to $C_{22}$ fatty acid, at least one hydroxy $C_{18}$ to $C_{20}$ fatty acid, or a combination thereof.

In some embodiments, the various suitable hydroxy fatty acids noted above can be saturated. In some embodiments, these hydroxy fatty acids can be predominantly saturated, i.e., greater than about 60% or greater than about 75% saturated.

In certain embodiments, the hydoxy fatty acid can be a $C_{16}$-$C_{26}$ hydoxy fatty acid and can be α-hydroxymyristic acid, β-hydroxymyristic acid, 3-hydroxy-β-methyltetradecanoic acid, α-hydroxypalmitic acid, β-hydroxypalmitic acid, 3-hydroxy-15-methylhexadecanoic acid, β-hydroxystearic acid, 12-hydroxystearic acid, and 17-hydroxystearic acid, or a mixture of any of the foregoing.

In certain embodiments, the solubilizing agent can comprise one or more glycol mono- or di-esters of a hydroxy $C_{16}$-$C_{26}$ fatty acid. Suitable glycols can include ethylene glycol, propylene glycol, and polyethylene glycol. In some embodiments, the solubilizing agent can comprise one or more polyethylene glycol mono- or di-esters of a hydroxy $C_{16}$-$C_{26}$ fatty acid. In some embodiments, the solubilizing agent can comprise one or more polyethylene glycol mono- or di-esters of a $C_{16}$-$C_{26}$ fatty acid. In some embodiments, the solubilizing agent comprises a mixture of one or more polyethylene glycol mono- and di-esters of a hydroxy $C_{16}$-$C_{26}$ fatty acid and one or more polyethylene glycol di-esters of a $C_{16}$-$C_{26}$ fatty acid. In some embodiments, the solubilizing agent comprises polyethylene glycol mono- and di-esters of 12-hydroxystearic acid and free polyethylene glycol (sold as KOLLIPHOR HS 15, available from BASF).

In certain embodiments, the pharmaceutical composition can comprise a first solubilizing agent comprising one or more polyethylene glycol mono-esters of a $C_6$-$C_{26}$ hydroxyfatty acid, one or more polyethylene glycol di-esters of a $C_6$-$C_{26}$ hydroxyfatty acid, or a combination thereof, and a second solubilizing agent.

In some embodiments, the second solubilizing agent can be TEFOSE 63 (mixture of PEG-6 stearate and ethylene glycol palmitostearate and PEG-32 stearate, available from GATTEFOSSÉ SAS, Saint-Priest, France), TEFOSE 1500 (mixture of PEG-6 stearate and PEG-32 stearate, available from GATTEFOSSÉ SAS, Saint-Priest, France), TEFOSE 2000 (mixture of PEG-6 stearate, ceteth-20, and stearath-20, available from GATTEFOSSÉ SAS, Saint-Priest, France), or GELOT 64 (mixture of PEG-75 stearate and glyceryl stearate, available from GATTEFOSSÉ SAS, Saint-Priest, France).

In certain embodiments, the second solubilizing agent can comprise one or more $C_6$-$C_{18}$ fatty acid PEG mono- or di-esters, one or more $C_6$-$C_{18}$ fatty acid mono-, di-, or tri-esters of glycerol, and combinations thereof. In one embodiment, the second solubilizing agent can be GELUCIRE 44/14.

In certain embodiments, the second solubilizing agent can comprise a castor oil or hydrogenated castor oil ethoxylate. In particular embodiments, the castor oil or hydrogenated castor oil ethoxylate can be KOLLIPHOR EL (polyethoxylated castor oil, available from BASF), KOLLIPHOR RH40 (polyoxyl 40 hydrogenated castor oil USP, available from BASF), MYRJ 52 (polyoxyl 40 stearate, available from Spectrum Chemical), ETOCAS 40 (polyoxyethylene (40) castor oil, available from Croda), LABRASOL (caprylocaproyl polyoxyl-8-glycerides NF and caprylocaproyl macrogol-8-glycerides EP, available from GATTEFOSSÉ SAS, Saint-Priest, France), or CRODURET 60 (PEG 60 hydrogenated castor oil, available from Croda).

In certain embodiments, the second solubilizer can comprise OVUCIRE 3460 (a mixture of hard fat, glyceryl ricinoleate, ceteth-20, and steareth-20, available from GATTEFOSSÉ, Saint-Priest, France) or OVUCIRE WL 3264 (hard fat polyoxyl 20 cetostearyl ether, available from GATTEFOSSÉ, Saint-Priest, France).

In some embodiments, the weight:weight ratio of the first solubilizing agent to the second solubilizing agent can range from 4:1 to about 10:1. In particular embodiments, the ratio of first solubilizing agent to second solubilizing agent can be about 9:1.

In some embodiments, the pharmaceutical composition can comprise a first solubilizing agent comprising one or more PEG esters of a $C_6$-$C_{26}$ hydroxy fatty acid, one or more PEG diesters of a $C_6$-$C_{26}$ hydroxy fatty acid, or a combination thereof; and a second solubilizing agent comprising a mixture polyoxylglycerides and glycols. In particular embodiments, the pharmaceutical composition can comprise a 9:1 (w:w) mixture of KOLLIPHOR HS 15 (polyethylene glycol mono- and di-esters of 12-hydroxystearic acid and free polyethylene glycol, available from BASF) and TEFOSE 63 (mixture of PEG-6 stearate and ethylene glycol palmitostearate and PEG-32 stearate, available from GATTEFOSSÉ SAS, Saint-Priest, France).

Propylene Glycol Monolaurate as a Solubilizing Agent

In certain embodiments, the solubilizing agent can comprise propylene glycol monolaurate (sold as LAUROGLYCOL 90, available from GATTEFOSSÉ SAS, Saint-Priest, France).

In some embodiments, the pharmaceutical composition can comprise propylene glycol monolaurate (sold as LAUROGLYCOL 90, available from GATTEFOSSÉ SAS, Saint-Priest, France) and a second solubilizing agent.

In some embodiments, the second solubilizing agent can be TEFOSE 63 (mixture of PEG-6 stearate and ethylene glycol palmitostearate and PEG-32 stearate, available from GATTEFOSSÉ SAS, Saint-Priest, France), TEFOSE 1500 (mixture of PEG-6 stearate and PEG-32 stearate, available from GATTEFOSSÉ SAS, Saint-Priest, France), TEFOSE 2000 (mixture of PEG-6 stearate, ceteth-20, and stearath-20, available from GATTEFOSSÉ SAS, Saint-Priest, France), or GELOT 64 (mixture of PEG-75 stearate and glyceryl stearate, available from GATTEFOSSÉ SAS, Saint-Priest, France).

In certain embodiments, the second solubilizing agent can comprise one or more $C_6$-$C_{18}$ fatty acid PEG mono- or di-esters, one or more $C_6$-$C_{18}$ fatty acid mono-, di-, or tri-esters of glycerol, and combinations thereof. In one embodiment, the second solubilizing agent can be GELUCIRE 44/14.

In certain embodiments, the second solubilizing agent can comprise a castor oil or hydrogenated castor oil ethoxylate. In particular embodiments, the castor oil or hydrogenated castor oil ethoxylate can be KOLLIPHOR EL (polyethoxylated castor oil, available from BASF), KOLLIPHOR RH40 (polyoxyl 40 hydrogenated castor oil USP, available from BASF), MYRJ 52 (polyoxyl 40 stearate, available from Spectrum Chemical), ETOCAS 40 (polyoxyethylene (40) castor oil, available from Croda), LABRASOL (caprylocaproyl polyoxyl-8-glycerides NF and caprylocaproyl macrogol-8-glycerides EP, available from GATTEFOSSÉ SAS, Saint-Priest, France), or CRODURET 60 (PEG 60 hydrogenated castor oil, available from Croda).

In certain embodiments, the second solubilizer can comprise OVUCIRE 3460 (a mixture of hard fat, glyceryl ricinoleate, ceteth-20, and steareth-20, available from GATTEFOSSÉ, Saint-Priest, France) or OVUCIRE WL 3264 (hard fat polyoxyl 20 cetostearyl ether, available from GATTEFOSSÉ, Saint-Priest, France).

In some embodiments, the weight:weight ratio of the first solubilizing agent to the second solubilizing agent can be from 4:1 to about 10:1. In particular embodiments, the ratio of first solubilizing agent to second solubilizing agent can be about 9:1 (w:w).

In some embodiments, the pharmaceutical composition can comprise propylene glycol monolaurate (sold as LAUROGLYCOL 90, available from GATTEFOSSÉ SAS, Saint-Priest, France) and a second solubilizing agent comprising polyoxyl 40 hydrogenated castor oil (sold as KOLLIPHOR RH40, available from BASF). In particular embodiments, the pharmaceutical composition can comprise a 9:1 mixture of LAUROGLYCOL 90 and KOLLIPHOR RH40

Methods of Treating Hormone Deficiencies

In addition to the compositions described above, this disclosure further provides methods for treating one or more conditions associated with hormone deficiency in a subject. The methods comprise vaginally administering to a subject in need thereof an effective amount of the pharmaceutical composition described herein.

In some embodiments, the condition being treated can be an estrogen deficiency in the vulvovaginal area, including conditions such as VVA.

In certain embodiments, the pharmaceutical composition can be administered once daily within in any of the above noted amounts until the disease or condition is treated.

In some embodiments, the method of treating the symptoms of VVA comprises administering a vaginal insert comprising the pharmaceutical composition described herein to the vagina of a subject in need thereof, wherein administering the vaginal insert does not require use of an applicator.

In some embodiments, the method of treating the symptoms of VVA comprises administering a vaginal insert comprising the pharmaceutical composition described herein to the vagina of a subject in need thereof, wherein administering the vaginal insert is by digital insertion.

In some embodiments, the method of treating the symptoms of VVA comprises administering a vaginal insert comprising the pharmaceutical composition described herein to the vagina of a subject in need thereof, wherein administering the vaginal insert is by insertion using an applicator.

In some embodiments, the method of treating the symptoms of VVA comprises administering a vaginal insert comprising the pharmaceutical composition described herein to the vagina of a subject in need thereof, wherein the vaginal insert is inserted about two inches into the vagina.

In some embodiments, the method of treating the symptoms of VVA comprises administering a vaginal insert comprising the pharmaceutical composition described herein to the vagina of a subject in need thereof, wherein administering the vaginal insert results in no or minimal subject irritation.

In some embodiments, the method of treating the symptoms of VVA comprises administering a vaginal insert comprising the pharmaceutical composition described herein to the vagina of a subject in need thereof, wherein subject irritation is selected from the group consisting of pain, itching, soreness, excessive discharge, swelling, or combinations thereof.

In some embodiments, the method of treating the symptoms of VVA comprises administering a vaginal insert comprising the pharmaceutical composition described herein to the vagina of a subject in need thereof, wherein subject irritation associated with administering the vaginal insert containing the API does not differ significantly from subject irritation associated with administering a placebo insert.

In some embodiments, the method of treating the symptoms of VVA comprises administering a vaginal insert comprising the pharmaceutical composition described herein to the vagina of a subject in need thereof, wherein subject irritation associated with administering the vaginal insert is reduced compared to subject irritation associated with administering other hormone replacement vaginal inserts.

In some embodiments, the method of treating the symptoms of VVA comprises administering a vaginal insert comprising the pharmaceutical composition described herein to the vagina of a subject in need thereof, wherein after two weeks of administration, the frequency of administering the vaginal insert is less frequent than that required by other hormone replacement vaginal inserts.

In some embodiments, the method of treating the symptoms of VVA comprises administering a vaginal insert comprising the pharmaceutical composition described herein to the vagina of a subject in need thereof, wherein time to ambulation for a subject is less than 20 minutes after administering the vaginal insert.

In some embodiments, the method of treating the symptoms of VVA comprises administering a vaginal insert comprising the pharmaceutical composition described herein to the vagina of a subject in need thereof, wherein time to ambulation for a subject is less than 10 minutes after administering the vaginal insert.

In some embodiments, the method of treating the symptoms of VVA comprises administering a vaginal insert comprising the pharmaceutical composition described herein to the vagina of a subject in need thereof, wherein time to ambulation for a subject is less than 5 minutes after administering the vaginal insert.

In some embodiments, the method of treating the symptoms of VVA comprises administering a vaginal insert comprising the pharmaceutical composition described herein to the vagina of a subject in need thereof, wherein time to ambulation for a subject after administering the vaginal insert is reduced compared to time to ambulation associated with administering other hormone replacement vaginal inserts.

In some embodiments, the method of treating the symptoms of VVA comprises administering a vaginal insert comprising the pharmaceutical composition described herein to the vagina of a subject in need thereof, wherein the vaginal insert can be administered when substantially no vaginal fluid is present in the vagina.

In some embodiments, the method of treating the symptoms of VVA comprises administering a vaginal insert comprising the pharmaceutical composition described herein to the vagina of a subject in need thereof, wherein the vaginal insert further comprises a capsule.

In some embodiments, the method of treating the symptoms of VVA comprises administering a vaginal insert comprising the pharmaceutical composition described herein to the vagina of a subject in need thereof, wherein the vaginal insert further comprises a capsule, wherein the capsule is substantially dissolved in the vagina. In some embodiments, at least about 90% of the capsule is dissolved in the vagina.

In some embodiments, the method of treating the symptoms of VVA comprises administering a vaginal insert comprising the pharmaceutical composition described herein to the vagina of a subject in need thereof, wherein the vaginal insert further comprises a capsule, wherein there is substantially no discharge of contents of the vaginal insert observed within 30 minutes after administering the vaginal insert.

In some embodiments, the method of treating the symptoms of VVA comprises administering a vaginal insert comprising the pharmaceutical composition described herein to the vagina of a subject in need thereof, wherein the vaginal insert further comprises a capsule, wherein there is substantially no discharge of contents of the vaginal insert observed within 2 hours after administering the vaginal insert.

In some embodiments, the method of treating the symptoms of VVA comprises administering a vaginal insert comprising the pharmaceutical composition described herein to the vagina of a subject in need thereof, wherein the vaginal insert further comprises a capsule, wherein the amount of discharge of contents of the vaginal insert is less than the amount of discharge observed with other hormone replacement vaginal inserts, as observed by visual examination.

Also provided is a method for enhancing subject compliance in a population of subjects having symptoms of VVA, comprising administering a vaginal insert comprising the pharmaceutical composition described herein, wherein the pharmaceutical composition comprises 1 microgram to 25 micrograms of estradiol, to the vagina of a subject in need thereof, wherein the subject administers the vaginal insert at least daily for two weeks.

In some embodiments, the present disclosure provides a method for enhancing subject compliance in a population of subjects having symptoms of VVA, the method comprising administering a vaginal insert comprising the pharmaceutical composition described herein to the vagina of a subject in need thereof, wherein the subject administers the vaginal insert daily for two weeks, and at least twice weekly thereafter.

In some embodiments, the present disclosure provides a method for enhancing subject compliance in a population of subjects having symptoms of VVA, the method comprising administering a vaginal insert comprising the pharmaceutical composition described herein to the vagina of a subject in need thereof, wherein compliance of subjects in the population administering the vaginal insert is enhanced compared to compliance of subjects in a population administering other hormone replacement vaginal inserts.

Figure 3A:
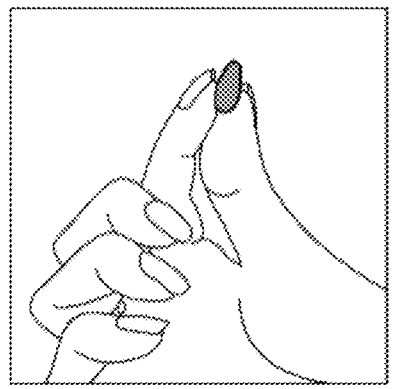
FIG. 3A shows an estradiol softgel capsule held with the larger end between the thumb and index fingers.
Figure 3B:
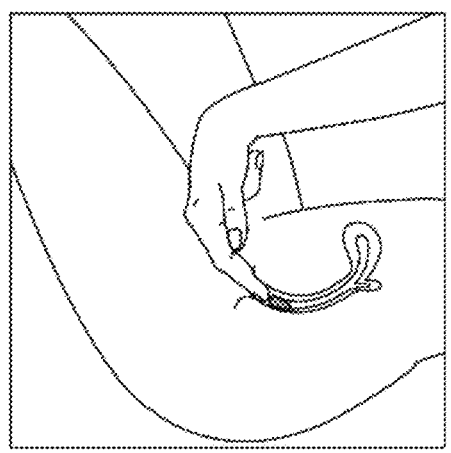
FIG. 3B shows insertion of an estradiol softgel capsule in a reclining position. The softgel is inserted into the lower third of the vagina with the smaller end up.
Figure 3C:
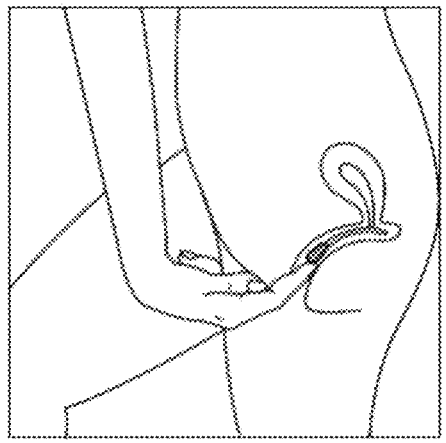
FIG. 3C shows insertion of an estradiol softgel capsule in a standing position. The softgel is inserted into the lower third of the vagina with the smaller end up.

In certain embodiments, the present disclosure provides a method for estrogenizing the vulva, which consists of the labia majora, the labia minora (labia majora and minora are collectively referred to as "the labia"), clitoris, vestibule of the vagina, bulb of the vestibule, and the glands of Bartholin (all of which can come into contact with the liquid that partially flows from the vagina). In some embodiments, an estradiol containing pharmaceutical composition can be digitally inserted about two inches into the vagina or inserted into the third of the vagina closest to the vaginal opening as shown in FIGS. 3A, 3B, and 3C. Without wishing to be bound to a particular theory, it is believed that the estradiol containing pharmaceutical composition dissolves, ruptures, or otherwise releases the pharmaceutical composition into the vagina, whereby the lower third of the vagina and labia are both reestrogenized. In some embodiments, the pharmaceutical composition is a liquid that partially flows to the labia and directly reestrogenizes the labia.

In certain embodiments, the present disclosure provides a method for avoiding transport of the estradiol to the uterus comprising administering an estradiol containing composition into the lower third of the vagina closest to the vaginal opening as shown in FIGS. 3A, 3B, and 3C. Without wishing to be bound by a particular theory, it is believed that the estradiol containing composition releases the estradiol in the lower third of the vagina, which substantially eliminates transport of the estradiol to the uterus, where unopposed estradiol can cause endometrial hyperplasia, which could potentially lead to endometrial cancer.

In certain embodiments, the present disclosure provides a method for estrogenizing the vulva. In some embodiments, the pharmaceutical composition is digitally inserted about two inches into the vagina or inserted into the third of the vagina closest to the vaginal opening as shown in FIGS. 3A, 3B, and 3C. Without wishing to be bound to a particular theory, it is believed that the gelatin capsule containing the pharmaceutical composition dissolves, ruptures, or otherwise releases the pharmaceutical composition into the vagina, whereby the lower third of the vagina and vulva are both reestrogenized. In some embodiments, the pharmaceutical composition can be a liquid that partially flows to the vulval tissue and directly reestrogenizes the vulva.

In certain embodiments, the present disclosure provides a method for treating VVA, including dyspareunia, vaginal dryness, and estrogen-deficient urinary states (including urinary tract infections), wherein a delivery vehicle comprising the pharmaceutical composition for treating VVA is digitally inserted approximately two inches into the vagina or into the third of the vagina closest to the opening of the vagina. This method can result in at least one of: improved compliance compared to other products for the treatment of VVA; improved user experience compared to other products for the treatment of VVA; and statistically significantly improved symptoms of VVA, compared to placebo or baseline within at least one, two, four, six, eight, ten, twelve, or more weeks after initiating administration. In certain embodiments, a method for the treatment of VVA, including dyspareunia, vaginal dryness, and estrogen-deficient urinary states (including urinary tract infections), is provided wherein a delivery vehicle containing a composition for the treatment of VVA in a tear drop shaped capsule as disclosed herein is inserted approximately two inches into the vagina or into the third of the vagina closest to the opening of the vagina. This method can result in at least one of: improved compliance compared to other products for the treatment of VVA; improved user experience compared to other products for the treatment of VVA; and statistically significantly improved symptoms of VVA, compared to placebo or baseline within at least one, two, four, six, eight, ten, twelve, or more weeks after initiation of administration.

Methods for Preparing the Pharmaceutical Compositions

In certain embodiments, the pharmaceutical composition can be prepared by blending estradiol with at least one pharmaceutically acceptable solubilizing agent. In certain embodiments, other excipients including, for example and without limitation, nontoxic pharmaceutically acceptable solvents, co-solvents, surfactants, lubricants, antioxidants, and/or other excipients suitable for vaginal delivery or absorption, and the like can be added to the pharmaceutical composition. In certain embodiments, the pharmaceutical composition can include sufficient solubilizing agent to fully solubilize the estradiol. It is expressly understood, however, the other volumes of solubilizing agent can be used depending on the level of estradiol solubilization desired. Persons of ordinary skill in the art will know and understand how to determine the volume of solubilizing agent and other excipients depending on the desired percent of estradiol to be solubilized in the pharmaceutical composition. In some embodiments, the solubilizing agent can be heated (for example, from about 40° C. to about 65° C.), although such heating is not necessary to dissolve the estradiol.

Delivery Vehicle

Generally, the pharmaceutical compositions described herein are delivered intravaginally inside of a delivery vehicle, for example a capsule. In certain embodiments, the capsules are soft capsules made of materials well-known in the pharmaceutical arts, for example, gelatin. However, in some embodiments, the delivery vehicle is integral with the pharmaceutical composition (i.e., the pharmaceutical composition is the delivery vehicle). In such embodiments the pharmaceutical compositions can be an insert, a gel, a cream, an ointment, a tablet, a suppository, or another preparation that is directly applied and absorbed vaginally.

In certain embodiments, the capsules do not contain one or more of the following: a hydrophilic gel-forming bioadhesive agent, a lipophilic agent, a gelling agent for the lipophilic agent, and/or a hydrodispersible agent. In certain embodiments, the capsules do not contain a hydrophilic gel-forming bioadhesive agent selected from: carboxyvinylic acid, hydroxypropylcellulose, carboxymethylcellulose, gelatin, xanthan gum, guar gum, aluminum silicate, and mixtures thereof. In certain embodiments, the capsules do not contain a lipophilic agent selected from: a liquid triglyceride, a solid triglyceride (with a melting point of about 35° C.), carnauba wax, cocoa butter, or mixtures thereof. In certain embodiments, the capsules do not contain a hydrophobic colloidal silica gelling agent. In certain embodiments, the capsules do not contain a hydrodispersible agent selected from: polyoxyethylene glycol, polyoxyethylene glycol 7-glyceryl-cocoate, or mixtures thereof. In some such embodiments, the liquid composition can be contained with a gelatin capsule as described herein. In some such embodiments, the capsule can comprise gelatin and optionally one or more further components selected from the group consisting of gelatin, hydrolyzed gelatin, sorbitol-sorbitan solution, water, glycerin, titanium dioxide, FD&C Red #40, ethanol, ethyl acetate, propylene glycol, polyvinyl acetate phthalate, isopropyl alcohol, polyethylene glycol, and ammonium hydroxide.

In certain embodiments, the delivery vehicle can be designed for ease of insertion. In certain embodiments, the delivery vehicle can be sized so that it can be comfortably inserted into the vagina. The delivery vehicle can be prepared in a variety of geometries. For example, the delivery vehicle can be shaped as a tear drop, a cone with frustoconical ends, a cylinder, a cylinder with larger "cap" portion, or in any other shape suitable for, and that eases insertion into, the vagina. In certain embodiments, the delivery vehicle can be used in connection with an applicator. In other embodiments, the delivery vehicle can be digitally inserted.

Figure 2:
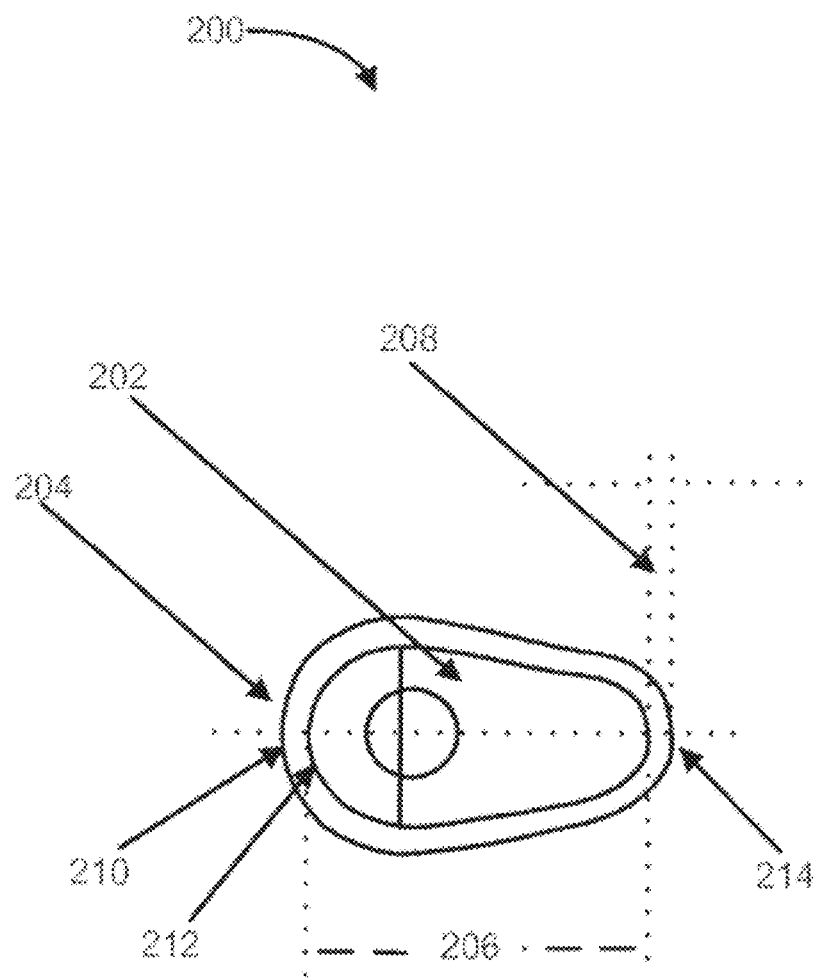
FIG. 2 illustrates a vaginal insert in accordance with various embodiments disclosed herein.

With reference to FIG. 2, delivery vehicle 200 includes pharmaceutical composition 202 and capsule 204. Width 208 represents the thickness of capsule 204, for example about 0.108 inches. The distance from one end of delivery vehicle 200 to another is represented by distance 206, for example about 0.690 inches. The size of delivery vehicle 200 can also be described by the arc swept by a radius of a given length. For example, arc 210, which is defined by the exterior of gelatin 204, is an arc swept by a radius of about 0.189 inches. Arc 212, which is defined by the interior of capsule 204, is an arc swept by a radius of about 0.0938 inches. Arc 214, which is defined by the exterior of gelatin 204 opposite arc 210, is an arc swept by a radius of about 0.108 inches. Suitable capsules of other dimensions can be provided. In certain embodiments, capsule 204 has dimensions the same as or similar to the ratios as provided above relative to each other. In some embodiments, the gelatin capsule can further comprise one or more components selected from the group consisting of hydrolyzed gelatin, sorbitol-sorbitan solution, water, glycerin, titanium dioxide, FD&C Red #40, ethanol, ethyl acetate, propylene glycol, polyvinyl acetate phthalate, isopropyl alcohol, polyethylene glycol, and ammonium hydroxide.

In certain embodiments, the delivery vehicle can be designed to remain in the vagina until the pharmaceutical composition is released. In certain embodiments, the delivery vehicle can dissolve intravaginally and can be absorbed into the vaginal tissue with the pharmaceutical composition, which can minimize vaginal discharge. In some embodiments, the delivery vehicle can be made from constituents that are nontoxic, for example, gelatin.

EXAMPLES

The pharmaceutical compositions described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1: Solubilizing Agents

Compositions having the ingredients shown in Table 1 were prepared by combining the ingredients using standard preparatory techniques.

TABLE 1

Estradiol Fill Formulas

| | A | B | C |
|---|---|---|---|
| Viscosity (cP) | 1418 | semi-solid | 37.5 |
| Composition/Component | % w/w | % w/w | % w/w |
| Estradiol | 0.008% w/w | 0.008% w/w | 0.008% w/w |
| Triacetin | 90% w/w | | |
| Kolliphor HS 15 (Solutol HS 15) | | 90% w/w | |
| Lauroglycol 90 | | | 90% w/w |
| Tefose 63 | 10% w/w | 10% w/w | |
| Kolliphor RH40 | | | 10% w/w |

Example 2: Pharmaceutical Composition

Estradiol was combined with one or more pharmaceutically acceptable solubilizing agents. The estradiol used in the pharmaceutical composition can be pharmaceutical grade, micronized estradiol, although other forms can also be used. The pharmaceutical composition included estradiol in a dosage strength of from about 1 μg to about 50 μg. The pharmaceutical composition can include 4 μg of estradiol. The pharmaceutical composition can include 10 μg of estradiol. The pharmaceutical composition can include 25 μg of estradiol.

The estradiol can be combined with pharmaceutically acceptable solubilizing agents as described herein, and, optionally, other excipients, to form a pharmaceutical composition.

Pharmaceutical compositions comprising one or more solubilizing agents as described herein that are liquid or semi-solid at room temperature can be tested using a Brookfield viscometer (Brookfield Engineering Laboratories, Middleboro, Mass.) at room temperature.

Pharmaceutical compositions comprising one or more solubilizing agents as described herein that are solid at room temperature can be assessed at 37° C. to determine their melting characteristics. The viscosity of the gels can be important during encapsulation of the formulation.

A dispersion assessment of the pharmaceutical compositions comprising one or more solubilizing agents as described herein can be performed. A dispersion assessment can be performed by transferring 300 mg of each vehicle system in 100 mL of 37° C. water, without agitation, and observing for mixing characteristics. Generally speaking, it is believed that formulations able to readily disperse in aqueous solution will have better dispersion characteristics upon administration.

Example 3: Delivery Vehicle

The pharmaceutical composition is delivered in a gelatin capsule delivery vehicle. The gelatin capsule delivery vehicle includes, for example, gelatin (e.g., Gelatin, NF (150 Bloom, Type B)), hydrolyzed collagen (e.g., GELITA, GELITA AG, Eberbach, Germany), glycerin, sorbitol special, or other excipients in proportions that are well known and understood by persons of ordinary skill in the art. Sorbitol special can be obtained commercially and can tend to act as a plasticizer and humectant.

A variety of delivery vehicles, Gels A through F, were developed, as shown in Table 2.

Example 4: Pharmaceutical Compositions with Delivery Vehicle

Various combinations of the pharmaceutical compositions comprising one or more solubilizing agents described herein and delivery vehicles of Table 2 can be prepared.

An aliquot of about 300 mg to about 310 mg of a pharmaceutical composition comprising one or more solubilizing agents as described herein can be prepared as described above. To encapsulate the vehicle system, each 300 mg to about 310 mg pharmaceutical composition aliquot can be encapsulated in about 200 mg of the gelatin capsule delivery vehicle. The aliquot size is arbitrary depending on the concentration of the estradiol and the desired gelatin capsule delivery vehicle size. Artisans will readily understand how to adjust the amount of estradiol in the pharmaceutical composition to accommodate a given size of delivery vehicle, when the delivery vehicle encapsulates the pharmaceutical composition.

Example 5: Process Using One or More Solubilizing Agents of the Present Disclosure FIG. 1 illustrates an embodiment of a method making a pharmaceutical composition comprising estradiol solubilized in a solubilizing agent comprising one or more solubilizing agents as described herein encapsulated in a soft gelatin delivery vehicle 100. In operation 102, the solubilizing agent(s) is heated to 40° C.±5° C. Heating can be accomplished through any suitable means. The heating can be performed in any suitable vessel, such as a stainless-steel vessel. Other pharmaceutical compositions can be made using the same general method by substituting various excipients, including the solubilizing agent.

TABLE 2

| | Gelatin Capsule Delivery Vehicles | | | | | |
|---|---|---|---|---|---|---|
| Ingredient | A % w/w | B % w/w | C % w/w | D % w/w | E % w/w | F % w/w |
| Gelatin, NF (150 Bloom, Type B) | 41.0 | 41.0 | 41.0 | 41.0 | 43.0 | 43.0 |
| Glycerin 99.7%, USP | 6.0 | 6.0 | 6.0 | 6.0 | 18.0 | 18.0 |
| Sorbitol Special, USP | 15.0 | 15.0 | 15.0 | 15.0 | — | — |
| GELITA (hydrolyzed collagen) | 3 | — | — | — | 3.0 | — |
| Citric acid | — | 0.1 | 0.5 | 1 | — | 0.1 |
| Purified Water | 35.0 | 37.9 | 37.5 | 37.0 | 36.0 | 38.9 |
| TOTAL | 100.0 | 100.0 | 100.0 | 100.0 | 100.0 | 100.0 |
| Dissolution gel strips, Avg. of 3 (500 mL, DH₂O, 50 rpm @ 37° C.) | 48 min (42, 45, 58) | 50 min (50, 51, 50) | 75 min (76, 75, 74) | 70 min (70, 71, 70) | — | — |
| Dissolution gel strips, Avg. of 3 (500 mL, pH 4 buffer, 50 rpm @ 37° C.) | 70 min | — | — | — | 78 min | 82 min |

Each delivery vehicle A through F was prepared at a temperature range from about 45° C. to about 85° C. Each molten delivery vehicle A through F was cast into a film, dried, and cut into strips. The strips were cut into uniform pieces weighing about 0.5 µg, with about 0.5 mm thickness. Strips were placed into a USP Type 2 dissolution vessel in either water or pH 4 buffer solution and the time for them to completely dissolve was recorded (see Table 3). Delivery vehicle A had the fastest dissolution in both water and pH 4 buffer solution.

In operation 104, GELUCIRE is mixed with the first solubilizing agent comprising to form the finished solubilizing agent. As used herein, any of the second solubilizing agents described herein can be used in operation 104 in place of GELUCIRE. Mixing is performed as would be known to persons of ordinary skill in the art, for example by impeller, agitator, stirrer, or other like devices used to mix pharmaceutical compositions. Operation 104 can be performed under an inert or relatively inert gas atmosphere, such as nitrogen gas. Mixing can be performed in any vessels that are known to persons of ordinary skill in the art, such as a stainless-steel vessel or a steel tank.

In operation 106 estradiol is mixed into the solubilizing agent. In embodiments, the estradiol is in a micronized form when mixed into the solubilizing agent. In other embodiments, the estradiol added is in a non-micronized form. Mixing can be facilitated by an impeller, agitator, stirrer, or other like devices used to mix pharmaceutical compositions. Operation 106 can be performed under an inert or relatively inert gas atmosphere, such as nitrogen gas.

In embodiments, however, the addition of estradiol can be performed prior to operation 104. In that regard, operations 104 and 106 are interchangeable with respect to timing or can be performed contemporaneously with each other.

In operation 110, the gelatin delivery vehicle is prepared. Any of the gelatin delivery vehicles described herein can be used in operation 110. In embodiments, gelatin, hydrolyzed collagen, glycerin, and other excipients are combined at a temperature range from about 45° C. to about 85° C. and prepared as a film. Mixing can occur in a steel tank or other container used for preparing gelatin delivery vehicles. Mixing can be facilitated by an impellor, agitator, stirrer, or other devices used to combine the contents of gelatin delivery vehicles. Operation 110 can be performed under an inert or relatively inert gas atmosphere, such as nitrogen gas. In embodiments, the gelatin delivery vehicle mixture is degassed prior to being used to encapsulate the pharmaceutical composition.

In operation 112, the gelatin delivery vehicle encapsulates the pharmaceutical composition, according to protocols well-known to persons of ordinary skill in the art. In operation 112, a soft gelatin capsule delivery vehicle is prepared by combining the pharmaceutical composition made in operation 106 with the gelatin delivery vehicle made in operation 110. The gelatin can be wrapped around the material, partially or fully encapsulating it or the gelatin can also be injected or otherwise filled with the pharmaceutical composition made in operation 106.

In embodiments, operation 112 is completed in a suitable die to provide a desired shape. Vaginal soft gel capsules can be prepared in a variety of geometries. For example, vaginal soft gel capsules can be shaped as a tear drop, a cone with frustoconical end, a cylinder, a cylinder with larger "cap" portion as illustrated in FIG. 2, or other shapes suitable for insertion into the vagina. The resulting pharmaceutical composition encapsulated in the soft gelatin delivery vehicle can be inserted digitally or with an applicator.

The breadth and scope of the present invention should not be limited by any of the above-described exemplary embodiments but should be defined only in accordance with the following claims and their equivalents.

All patents, patent applications, and other references noted or referenced in this application are hereby incorporated by reference in their entirety.

What is claimed is:

1. A vaginal insert comprising a therapeutically effective amount a composition comprising from about 1 microgram to about 25 micrograms of estradiol; and a solubilizing agent, wherein the solubilizing agent comprises at least one C2-C5 fatty acid or a glycol ester, monoglyceride, diglyceride, or triglyceride thereof, wherein the viscosity of the composition is about 5 cP to about 3000 cP at room temperature, wherein the insert further comprises a capsule encapsulating the therapeutically effective amount of estradiol and the solubilizing agent.

2. The vaginal insert of claim 1, further comprising a second solubilizing agent selected from the group consisting of a mixture of PEG-6 stearate, ethylene glycol palmitostearate, and PEG-32 stearate; a mixture of hard fat, glyceryl ricinoleate, ceteth-20, and steareth-20; polyoxyl 40 hydrogenated castor oil USP; hard fat polyoxyl 20 cetostearyl ether; and combinations thereof.

3. The vaginal insert of claim 2, wherein the second solubilizing agent is a mixture of PEG-6 stearate, ethylene glycol palmitostearate, and PEG-32 stearate.

4. The vaginal insert of claim 1, wherein the solubilizing agent comprises at least one C3 fatty acid or a glycol mono- or di-ester thereof, a monoglyceride, diglyceride, or triglyceride thereof, or a combination of any of the foregoing.

5. A method of treating an estrogen-deficient state, comprising administering to a female in need thereof, the vaginal insert of claim 1.

6. The method of claim 5, wherein the estrogen-deficient state is selected from the group consisting of vulvovaginal atrophy, dysuria, dyspareunia, estrogen-deficient urinary state, and vaginal bleeding associated with sexual activity.

7. A vaginal insert comprising:
(a) a therapeutically effective amount of estradiol;
(b) a first solubilizing agent comprising one or more polyethylene glycol mono- or di-esters of a hydroxy C16-C26 fatty acid; and
(c) a second solubilizing agent comprising a mixture of PEG-6 stearate, ethylene glycol palmitostearate, and PEG-32 stearate.

8. The vaginal insert of claim 7, wherein the therapeutically effective amount of estradiol is from about 1 microgram to about 25 micrograms.

9. The vaginal insert of claim 7, wherein the insert further comprises a capsule encapsulating the estradiol, the first solubilizing agent, and the second solubilizing agent.

10. A method of treating an estrogen-deficient state, comprising administering to a female in need thereof, the vaginal insert of claim 7.

11. The method of claim 10, wherein the estrogen-deficient state is selected from the group consisting of vulvovaginal atrophy, dysuria, dyspareunia, estrogen-deficient urinary state, and vaginal bleeding associated with sexual activity.

12. A vaginal insert comprising a composition comprising:
(d) about 1 microgram to about 25 micrograms estradiol;
(e) a first solubilizing agent comprising propylene glycol monolaurate; and
(f) a second solubilizing agent comprising polyoxyl 40 hydrogenated castor oil USP.

13. The vaginal insert of claim 12, wherein the viscosity of the composition is about 5 cP to about 3000 cP at room temperature.

14. The vaginal insert of claim 12, wherein the insert further comprises a capsule encapsulating the estradiol, the first solubilizing agent, and the second solubilizing agent.

15. A method of treating an estrogen-deficient state, comprising administering to a female in need thereof, the vaginal insert of claim 12.

16. The method of claim 15, wherein the estrogen-deficient state is selected from the group consisting of vulvovaginal atrophy, dysuria, dyspareunia, estrogen-deficient urinary state, and vaginal bleeding associated with sexual activity.

* * * * *